(12) United States Patent
Hart et al.

(10) Patent No.: US 12,201,075 B2
(45) Date of Patent: Jan. 21, 2025

(54) **METHODS AND COMPOSITIONS FOR AXILLARY SHOOT MICROPROPAGATION OF *CANNABIS* AND RELATED PLANTS**

(71) Applicants: JUSHI IP, LLC, Boca Raton, FL (US); PHYTOTECH LABS, INC., Lenexa, KS (US)

(72) Inventors: David S. Hart, Lenexa, KS (US); Jonathan McGiveron, Sparks, NV (US); Michael Kane, Gainesville, FL (US)

(73) Assignees: Jushi IP, LLC, Boca Raton, FL (US); Phytotech Labs, Inc., Lenexa, KS (US)

( * ) Notice: Subject to any disclaimer, the term of this patent is extended or adjusted under 35 U.S.C. 154(b) by 0 days.

(21) Appl. No.: 17/500,864

(22) Filed: Oct. 13, 2021

(65) Prior Publication Data
US 2022/0110278 A1      Apr. 14, 2022

Related U.S. Application Data

(60) Provisional application No. 63/091,181, filed on Oct. 13, 2020.

(51) Int. Cl.
*A01H 4/00*      (2006.01)
*A01H 6/28*      (2018.01)

(52) U.S. Cl.
CPC .............. *A01H 4/008* (2013.01); *A01H 4/005* (2013.01); *A01H 6/28* (2018.05)

(58) Field of Classification Search
CPC ................................ A01H 4/008; A01H 4/005
See application file for complete search history.

(56) References Cited

U.S. PATENT DOCUMENTS

| | | | |
|---|---|---|---|
| 5,563,055 | A | 10/1996 | Townsend et al. |
| 8,541,653 | B2 | 9/2013 | Olhoft et al. |
| 9,228,209 | B2 * | 1/2016 | Steward ............... A61P 17/00 |
| 9,699,977 | B2 | 7/2017 | Laine et al. |
| 2008/0196121 | A1 | 8/2008 | Murali et al. |
| 2009/0083883 | A1 | 3/2009 | Arias et al. |
| 2012/0156784 | A1 | 7/2012 | Adams, Jr. et al. |
| 2019/0387697 | A1 | 12/2019 | Grace et al. |
| 2020/0196548 | A1 | 6/2020 | Whitton |

FOREIGN PATENT DOCUMENTS

| | | | |
|---|---|---|---|
| CN | 1887043 B | 8/2010 | |
| CN | 103141389 A | 6/2013 | |
| CN | 107736251 A | 2/2018 | |
| GB | 2568032 A | 5/2019 | |
| WO | 94/02620 A3 | 2/1994 | |
| WO | WO-2019006466 A1 * | 1/2019 | ............ A01G 22/15 |
| WO | WO-2019006470 A1 * | 1/2019 | ............ A01H 4/005 |
| WO | 2019217843 A1 | 11/2019 | |
| WO | 2021034755 A1 | 2/2021 | |

OTHER PUBLICATIONS

Mcguiness et al (The Role of Gibberellins and Brassinosteroids in Nodulation and Arbuscular Mycorrhizal Associations. Frontiers in Plant Science. 1-7, 2019) (Year: 2019).*
Kieber et al (Cytokinins. The *Arabidopsis* Book. 1-35, 2014) (Year: 2014).*
Greenboim-Wainberg (Cross Talk between Gibberellin and Cytokinin: The *Arabidopsis* GA Response Inhibitor Spindly Plays a Positive Role in Cytokinin Signaling. The Plant Cell, vol. 17, 92-102, Jan. 2005) (Year: 2005).*
Schiller et al (Effect of trans-zeatin riboside application on growth of banana (Musa AAA Simmonds) cv. Williams in the juvenile phase. Revista Colombiana De Ciencias Hortícolas—vol. 13 No. 2, pp. 161-170, May-Aug. 2019 (Year: 2019).*
Hu et al (Gibberellins Promote Brassinosteroids Action and Both Increase Heterosis for Plant Height in Maize (*Zea mays* L.) Frontiers in Plant Science, 1-17, 2017). (Year: 2017).*
Banerjee et al (Efficient production of transgenic potato (*S. tuberosum* L. ssp. *andigena*) plants via Agrobacterium tumefaciens-mediated transformation. Plant Science 170. 732-738, 2006) (Year: 2006).*
Murashige and Skoog Salt and Vitamin Mixture_Thermo Fisher Scientific (2022) (Year: 2022).*
Colmenero-Flores et al (Chloride as a Beneficial Macronutrient in Higher Plants: New Roles and Regulation. Int. J. Mol. Sci., 20, 1-32, 2019). (Year: 2019).*
Galan-Avila et al (Development of a Direct in vitro Plant Regeneration Protocol from *Cannabis sativa* L. Seedling Explants: Developmental Morphology of Shoot Regeneration and Ploidy Level of Regenerated Plants. Frontiers in Plant Science. 1-15, May 2020). (Year: 2020).*
Page et al (Basal media optimization for the micropropagation and callogenesis of *Cannabis sativa* L.). published Feb. 9, 2020). (Year: 2020).*
PCT Invitation to Pay Additional Fees dated Dec. 21, 2021, International Application No. PCT/US21/54862, pp. 1-2.

(Continued)

*Primary Examiner* — Charles Logsdon
*Assistant Examiner* — Wayne Zhong
(74) *Attorney, Agent, or Firm* — Siepmann IP, PLLC

(57) ABSTRACT

A plant medium composition and methodology of application of the medium as it pertains to the micropropagation of *Cannabis* and related plant species is described that yields two to four-fold increase in the number of biologically functional nodes from axillary shoots thereby allowing for exponential amplification of such plant species. The compositions comprise basal plant media supplemented with: (i) one or more cytokinins, and (ii) one or more gibberellins and/or brassinolides. This achievement in exponential shoot growth of these plant species represents a marked step forward in the *Cannabis* industry as it pertains to commercial micropropagation of a recreationally and medicinally important plant whose extracts are the subject of numerous clinical trials.

19 Claims, 21 Drawing Sheets

(56) References Cited

OTHER PUBLICATIONS

Ruth Y. Schmitz et al., "Cytokinins: Synthesis and Biological Activity of Geometric and Position Isomers of Zeatin," Plant Physiol., vol. 50, 1972, pp. 702-705.

Willem F. Wolkers et al. (editors), "Cryopreservation and Freeze-Drying Protocols," Humana Press, 2015, pp. 1-730.

Sae Shimizu-Sato et al., "Auxin-cytokinin interactions in the control of shoot branching," Plant Mol Biol, vol. 69, 2009, pp. 429-435.

Cheng Chaohua et al., "A rapid shoot regeneration protocol from the cotyledons of hemp(*Cannabis sativa* L.)," Industrial Crops and Products, vol. 83, 2016, pp. 61-65.

Folke Skoog et al., "Chemical Regulation of Growth and Organ Formation in Plant Tissues Cultured In Vitro," Vitro Symp Soc Exp Biol, 1957, pp. 118-131.

Aurelia Slusarkiewicz-Jarzina et al., "Influence of Cultivar, Explant Source and Plant Growth Regulartor on Callus Induction and Plant Regeneration of *Cannabis sativa* L.," Acta Biol. Crac. Ser. Bot., vol. 47, No. 2, 2005, pp. 145-151.

Kaoru Sugimoto et al., "*Arabidopsis* Regeneration from Multiple Tissues Occurs via a Root Development Pathway," Developmental Cell, vol. 18, Mar. 2010, pp. 463-471.

Milos Tanurdzic et al., "Epigenomic Consequences of Immortalized Plant Cell Suspension Culture, " PLOS Biology, vol. 6, Issue 12, Dec. 2008, pp. 2880-2895.

Kenneth V. Thimann et al., "On the Inhibition of Bud Development and other Functions of Growth Substance in Vicia Faba," Proceedings of the Royal Society of London. Series B, Containing Papers of a Biological Character 114.789, 1934, pp. 317-339.

Y. V. Ukhatova et al., "Cryopreservation of red raspberry cultivars from the VIR in vitro collection using a modified droplet vitrification method," In Vitro Cell.Dev.Biol.-Plant, vol. 53, 2017, pp. 394-401.

Mikihisa Umehara et al., "Inhibition of shoot branching by new terpenoid plant hormones," Nature, vol. 455, Sep. 2008, pp. 195-201.

Ren Wang et al., "A Micropropagation System for Cloning of Hemp (*Cannabis sativa* L.) by Shoot Tip Culture," Pak. J. Bot., vol. 31, No. 2, 2009, pp. 603-608.

David Weiss et al., "Mechanisms of Cross Talk between Gibberellin and Other Hormones," Plant Physiology, vol. 144, Jul. 2007, pp. 1240-1246.

Yan O. Zubo et al., "Role of the Cytokinin-Activated Type-B Response Regulators in Hormone Crosstalk," Plants, vol. 9, No. 166, 2020, pp. 1-18.

Christine Richez-Dumanois et al., "Multiplication végétative in vitro du chanvre (*Cannabis sativa* L.). Application à la conservation des clones sélectionnés," Agrnomie, vol. 6, No. 5, 1986, pp. 487-495. (Includes Machine-Generated English Translation).

Alexander Betekhtin et al., "Nuclear genome stability in long-term cultivated callus lines of Fagopyrum tataricum (L.) Gaertn," PLOS One, DOI:10.1371/journal.pone.0173537, Mar. 9, 2017, pp. 1-17.

Christine A. Beveridge et al., "The shoot controls zeatin riboside export from pea roots. Evidence from the branching mutant rms4," The Plant Journal, vol. 11, No. 2, 1997, pp. 339-345.

Judith K. Booth et al., "Terpene synthases from *Cannabis sativa*," PLOS One, https://doi.org/10.1371/journal.pone.0173911, Mar. 29, 2017, pp. 1-20.

Philip B. Brewer et al., "Strigolactone Acts Downstream of Auxin to Regulate Bud Outgrowth in Pea and *Arabidopsis*," Plant Physiology, vol. 150, May 2009, pp. 482-493.

Suman Chandra et al., "Propagation of Cannabis for Clinical Research: An Approach Towards a Modern Herbal Medicinal Products Development," Frontiers in Plant Science, vol. 11, Article 958, Jun. 2020, pp. 1-10.

Laurent Corbesier et al., "Cytokinin levels in leaves, leaf exudate and shoot apical meristem of *Arabidopsis thaliana* during floral transition," Journal of Experimental Botany, vol. 54, No. 392, Nov. 2003, pp. 2511-2517.

S.R.G. Page et al., "Basal media optimization for the micropropagation and callogenesis of *Cannabis sativa* L.," BioRxiv, 2020, pp. 1-23.

PhytoTechnology Laboratories, Product Information Sheet for DKW Basal Salt Mixture, Retrieved from the Internet: www.phytotechlab.com, May 2014, 1 Page.

John A. Driver et al., "In vitro propagation of Paradox Walnut root stock," HortScience, vol. 19(4), Aug. 1984, pp. 507-509.

Michael B. Greenway et al., "A nutrient medium for diverse applications and tissue growth of plant species in vitro," Vitro Cell. Dev. Biol.-Plant, vol. 48, 2012, pp. 403-410.

M. Feeney et al., "Tissue Culture and Agrobacterium-Mediated Transformation of Hemp (*Cannabis sativa* L.)," Vitro Cell. Dev. Biol.-Plant, vol. 39, Nov.-Dec. 2003, pp. 578-585.

Sonal Mishra et al., "The Role of Strigolactones and Their Potential Cross-talk under Hostile Ecological Conditions in Plants," Frontiers in Physiology, vol. 7, Article 691, Jan. 2017, pp. 1-7.

Alberto Galan-Avila et al., "Development of a Direct in vitro Plant Regeneration Protocol From *Cannibis sativa* L. Seedling Explants: Developmental Morphology of Shoot Regeneration and Ploidy Level of Regenerated Plants," Frontiers in Plant Science, vol. 11, Article 645, May 2020, pp. 1-15.

O. L. Gamborg et al., "Nutrient Requirements of Suspension Cultures of Soybean Root Cells," Experimental Cell Research, vol. 50, 1968, pp. 151-158.

Victoria Gomez-Roldan et al., "Strigolactone inhibition of shoot branching," Nature, vol. 455, Sep. 2008, pp. 189-195.

Norman E. Good et al., "Hydrogen Ion Buffers for Biological Research," Biochemistry, vol. 5, No. 2, Feb. 1966, pp. 467-477.

Marie Grulichova et al., "Effect of Different Phytohormones on Growth and Development of Micropropagated *Cannabis sativa* L.," Conference Paper for Mendel Net, Nov. 2017, pp. 618-623.

Carl E. Hansen et al., "Concentration Gradients of trans-Zeatin Riboside and trans-Zeatin in Maize Stem," Plant Physiology, vol. 75, 1984, pp. 959-963.

Naoya Hirose et al., "Regulation of cytokinin biosynthesis, compartmentalization and translocation," Journal of Experimental Botany, vol. 59, No. 1, 2008, pp. 75-83.

D. R. Hoagland et al., "The Water-Culture Method for Growing Plants without Soil," Circular. California agricultural experiment station 347.2nd edit (1950).

Hong-Jiu Liu et al., "Response of axillary bud development in garlic (*Allium sativum* L.) to seed cloves soaked in gibberellic acid (GA3) solution," Journal of Integrative Agriculture, vol. 19, No. 4, 2020, pp. 1044-1054.

R. Horgan et al., "A New Cytokinin from Populus x Robusta," Phytochemistry, vol. 14, 1975, pp. 1005-1008.

Shinsaku Ito et al., "Regulation of Strigolactone Biosynthesis by Gibberellin Signaling," Plant Physiology, vol. 174, Jun. 2017, pp. 1250-1259.

Takatoshi Kiba et al., "Side-Chain Modification of Cytokinins Controls Shoot Growth in *Arabidopsis*," Developmental Cell, vol. 27, Nov. 2013, pp. 452-461.

Hemant Lata et al., "Propagation through alginate encapsulation of axillary buds of *Cannabis sativa* L.—an important medicinal plant," Physiol. Mol. Biol. Plants, 15(1), Jan. 2009, pp. 79-86.

Hemant Lata et al., "In vitro mass propagation of *Cannabis sativa* L.: A protocol refinement using novel aromatic cytokinin meta-topolin and the assessment of eco-physiological, biochemical and genetic fidelity of micropropagated plants," Journal of Applied Research on Medicinal and Aromatic Plants, vol. 3, 2016, pp. 18-26.

Hemant Lata et al., "Thidiazuron-induced high-frequency direct shoot organogenesis of *Cannabis sativa* L.," In Vitro Cell.Dev.Biol.-Plant, vol. 45, 2009, pp. 12-19.

Nelson J. Leonard et al., "Cytokinins: Synthesis, Mass Spectra, and Biological Activity of Compounds Related to Zeatin," Proceedings of the National Academy of Sciences, vol. 63, No. 1, 1969, pp. 175-182.

J. D. Litvay et al., "Conifer Suspension Culture Medium Development Using Analytical Data from Developing Seeds," IPC Technical Paper Series, No. 115, Nov. 1981, pp. 1-18.

Gregory Lloyd et al., "Commercially-Feasible Micropropagation of Mountain Laurel, Kalmia Latifolia, by Use of Shoot-Tip Culture,"

(56) References Cited

OTHER PUBLICATIONS

Commercially-feasible micropropagation of mountain laurel, *Kalmia latifolia*, by use of shoot-tip culture, vol. 30, pp. 421-427.
Jessica D. Lubell-Brand et al., "An In Vitro-Ex Vitro Micropropagation System for Hemp," HortTechnology, vol. 31, No. 2, Apr. 2021, pp. 199-207.
Lewis N. Mander, "Twenty years of gibberellin research," Nat. Prod. Rep., vol. 20, 2003, pp. 49-69.
Špela Mestinšek Mubi et al., "In vitro Tissue Culture and Genetic Analysis of Two High-CBD Medical Cannabis (*Cannabis sativa* L.) Breeding Lines," Genetika, vol. 52, No. 3, 2020, pp. 925-941.
Tomasz Wrobel et al., "Modified Nodal Cuttings and Shoot Tips Protocol for Rapid Regeneration of *Cannabis sativa* L.," Journal of Natural Fibers, 2020, pp. 1-10.
Panagiota-Kyriaki Revelou et al., "Identification of Auxin Metabolites in Brassicaceae by Ultra-Performance Liquid Chromatography Coupled with High-Resolution Mass Spectrometry," Molecules, vol. 24, No. 2615, 2019, pp. 1-21.
Adrian S. Monthony et al., "Recalcitrance of *Cannabis sativa* to de novo regeneration; a multi-genotype replication study," PLOS One, vol. 16, No. 8, Aug. 2021, e0235525, pp. 1-28.
PhytoTechnology Laboratories, Product Information Sheet for Murashige & Skoog (MS) Modified Basal Medium w/ Gamborg Vitamins, Retrieved from the Internet: www.phytotechlab.com, Mar. 2014, 1 Page.
Toshio Murashige et al., "A Revised Medium for Rapid Growth and Bio Assays with Tobacco Tissue Cultures," Physiologia Plantarum, vol. 15, 1962, pp. 473-497.
Jun Ni et al., "Gibberellin Promotes Shoot Branching in the Perennial Woody Plant *Jatropha curcas*," Plant & Cell Physiology, vol. 56, No. 8, 2015, pp. 1655-1666.
Iva Smykalova et al., "The effects of novel synthetic cytokinin derivatives and endogenous cytokinins on the in vitro growth responses of hemp (*Cannabis sativa* L.) explants," Plant Cell, Tissue and Organ Culture (PCTOC), vol. 139, 2019, pp. 381-394.
E.C. Pua et al. (editors), Transgenic Crops VI, vol. 61, Biotechnology in Agriculture and Forestry, Springer Science & Business Media, 2007, pp. 1-442.
Asami Osugi et al., "Systemic transport of trans-zeatin and its precursor have differing roles in *Arabidopsis* shoots," Nature Plants, vol. 3, Article 17112, Jul. 2017, pp. 1-6.
David S. Hart, "New Plant Growth Regulators and an Update on Established Plant Growth Regulators," In Vitro Cellular & Developmental Biology-Animal, vol. 54, 233 Spring St, New York, NY 10013 USA: Springer, Jun. 2018, pp. 1-33.
Jessica L. Parsons et al., "Polyploidization for the Genetic Improvement of *Cannabis sativa*," Frontiers in Plant Science, vol. 10, Article 476, Apr. 2019, pp. 1-12.
M. Quoirin et al., "Improved media for in vitro culture of *Prunus* sp.," Symposium on Tissue Culture for Horticultural Purposes 78, 1977, pp. 437-442.
Thomas Regnault et al., "The gibberellin precursor GA12 acts as a long-distance growth signal in *Arabidopsis*," Nature Plants, Article 15073, Jun. 2015, pp. 1-9.
David L. Richer, "Synergism—a Patent View," Pestic. Sci., vol. 19, 1987, pp. 309-315.
E. Rugini, "In Vitro Propagation of Some OLIVE (*Olea europaea sativa* L.) Cultivars with Different Root-Ability, and Medium Development Using Analytical Data from Developing Shoots and Embryos," Scientia Horticulturae, vol. 24, 1984, pp. 123-134.
Hanna Rybicka et al., "Zeatin in *Cannabis* Fruit," Phytochemistry, vol. 13, 1974, pp. 282-283.
Roy U. Schenk et al., "Medium and techniques for induction and growth of monocotyledonous and dicotyledonous plant cell cultures," Canadian Journal of Botany, vol. 50, 1972, pp. 199-204.
PCT International Search Report and Written Opinion dated Mar. 2, 2022, International Application No. PCT/US2021/054862, pp. 1-10.
Yuan et al., "Regulation of 2, 4-epibrassinolide on mineral nutrient uptake and ion distribution in Ca (NO3) 2 stressed cucumber plants." Journal of plant physiology 188 (2015): 29-36.
Jan Adriaan Rossouw, "Effect of cytokinin and gibberellin on potato tuber dormancy," Diss. University of Pretoria, 2008, pp. 1-93.

\* cited by examiner

METHODS AND COMPOSITIONS FOR AXILLARY SHOOT MICROPROPAGATION OF *CANNABIS* AND RELATED PLANTS

BACKGROUND

The field of medicinal and recreational use of *Cannabis* has grown substantially the last six years with several states legalizing recreational-use marijuana. Legal sales of cannabis are projected to be $30 billion by 2025. (See, Dorbian, Iris, Forbes, Sep. 24, 2019, "New *Cannabis* Report Predicts Legal Sales to Reach Nearly $30 Billion by 2025."). Public interest in non-intoxicating medicinal compounds from hemp, specifically cannabidiols (CBDs), has grown significantly in the nutraceutical industry, as well as the pharmaceutical industry, with one drug already gaining two FDA approvals for separate medical indications (EPIDIOLEX® (cannabidiol), Greenwich Biosciences, CA, US, for the treatment of seizures associated with Lennox-Gastaut syndrome or Dravet syndrome in patients 2 years of age and older and seizures associated with the rare genetic disease tuberous sclerosis complex in patients 1 year of age and older). There are also currently over 250 on-going clinical trials in the United States focused on the use of cannabidiols for treatment of various medical indications. (See, clinicaltrials.gov).

Micropropagation is defined as the rapid clonal propagation of plants from tissues, usually shoot-tips or axillary buds, cultured aseptically in vessels on defined media under controlled light and temperature. The current state of the art in the commercial micropropagation of *Cannabis* cultivars in vitro is achieved through node culture using micropropagation techniques, or more infrequently via regeneration indirectly from callus. (See, Wang et al., *Pak. J. Bot.*, 41(2):603-608, 2009; Slusarkiewicz-Jarzina et al., *ACTA Biol. Cracov. Series Botanica*, 47/2:145-151, 2005; and Lata et al., *In Vitro Cell. Dev. Biol.-Plant*, 45:12-19, 2009). However, node culture is well known in the field to be a relatively inefficient process. Many commercially valuable crops are more efficiently produced via shoot culture, the clonal production of plants via enhanced axillary shoot proliferation in the presence of plant growth regulators (PGRs), especially cytokinin, in the culture medium. (See, Kane, "Propagation by Shoot Culture," Plant Tissue Culture, Development and Biotechnology; Triguano and Gray, Eds; CRC Press, 2011). Micropropagation via shoot culture is a more efficient and ideal method of generating more shoots as compared with node culture and can yield exponential shoot multiplication.

For *Cannabis* cultivars there are no known published methods to date that clearly demonstrate PGR-enhanced axillary shoot proliferation. This has been a stumbling block to progress and mass production in the industry for many years. While a few publications have alleged axillary shoot formation in *Cannabis*, these publications have not demonstrated this achievement over repeated subcultures in vitro, a key aspect to maintain micropropagation on a continual basis and critical for efficient commercial application. (See, Lata et al., *J. Appl. Res. Med. Arom. Plants*, 3:18-26, 2016; Richez-Dumanois et al., *Argonomie*, 6(5):487-495,1986; Wróbel et al., *J. Nat. Fibers*, DOI: 10.1080/15440478.2020.1748160, 2020; and Smýkalová et al., *Plant Cell, Tissue and Organ Culture*, 139:381-394, 2019).

In the field of Cannabaceae micropropagation there exists a stark knowledge gap that precludes exponential growth of cultivars in an industrially and/or commercially cost-effective manner. While many of the usual pathways for micropropagation have been attempted, the results have been mixed and when hints of success appear they are either not reproducible across multiple subcultures or between other species. To form axillary shoots, and to overcome the production inefficiencies in the *Cannabis* micropropagation industry, new methodologies were employed as described herein. For the first time, successful repeated in vitro subcultures of plants producing axillary shoots was achieved in *Cannabis*. These new methodologies include an optional initial cleansing growth step, followed by shoot formation on PGR-spiked basal plant medium. Described herein are new plant culture medium formulations for this purpose as well as key methodologies integral to promote sustained axillary shoot micropropagation for the first time in *Cannabis*.

SUMMARY

Described herein are compositions and methods for axillary shoot micropropagation of various Cannabaceae plant species including *Cannabis*.

The compositions are intended to be plant media and comprise a basal plant medium supplemented with certain quantities of: (i) one or more cytokinins, and (ii) one or more gibberellins and/or brassinolides. In one embodiment, the plant media compositions comprise at least one cytokinin and at least one gibberellin.

The basal plant medium is not particularly limited, and in various embodiments is selected from one or more of Murashige and Skoog (MS) media, Driver Kuniyaki Walnut (DKW) media, Lloyd and McCown Woody plant media (WPM), Schenk and Hildebrandt media, Gamborgs B-5 media, BABI media, Chu's N6 media, Quoirin & Lepoivre media, Litvay media, Hoaglands media, Anderson media, and Gresshoff & Doy media.

In the described compositions, the supplemented cytokinin is one or more of a cytokinin base, a riboside, and/or a riboside-5'-monophosphate. In certain embodiments where the cytokinin is a cytokinin base, the cytokinin base is selected from at least 6-(3,3-dimethylallylaminopurine, 6-(E)-4-hydroxy-3-methylbut-2-enylaminopurine, 6-(3-hydroxybenzylaminopurine, 6-(4-hydroxy-3-methylbutylaminopurine, 6-((Z)-4-hydroxy-3-methylbut-2-enylaminopurine, 6-benzylaminopurine, and 6-furfurylaminopurine. In certain embodiments, where the cytokinin is a riboside, then the ribose is selected from one or more of 6-(3,3-dimethylallylamino)-9-β-D-ribofuranosylpurine, 6-((E)-4-hydroxy-3-methylbut-2-enylamino)-9-β-D-ribofuranosylpurine, 6-(3-hydroxybenzylamino)-9-b-D-ribofuranosylpurine, 6-(4-hydroxy-3-methylbutylamino)-9-β-D-ribofuranosylpurine, 6-((Z)-4-hydroxy-3-methylbut-2-enylamino)-9-β-D-ribofuranosylpurine, 6-benzylamino-9-β-D-ribofuranosylpurine, and 6-furfurylamino-9-β-D-ribofuranosylpurine. Likewise, in certain embodiments wherein the medium comprises a riboside-5'-phosphate as the cytokinin, the cytokinin is selected from one or more of 6-(3,3-dimethylallylamino)-9-b-D-ribofuranosylpurine-5'-monophosphate disodium monohydrate, 6-((E)-4-hydroxy-3-methylbut-2-enylamino)-9-β-D-ribofuranosylpurine-5'-monophosphate disodium monohydrate, 6-(3-hydroxybenzylamino)-9-β-D-ribofuranosylpurine-5'-monophosphate disodium monohydrate, 6-(4-hydroxy-3-methylbutylamino)-9-β-D-ribofuranosyl purine-5'-monophosphate disodium monohydrate, 6-((Z)-4-hydroxy-3-methylbut-2-enylamino)-9-β-D-ribofuranosylpurine-5'-monophosphate disodium monohydrate, 6-benzylamino-9-β-D-ribofuranosylpurine-5'-monophosphate, and 6-furfurylamino-9-β-D-ribofuranosylpurine-5'-monophosphate.

The plant medium compositions described herein are in the form of a powder, liquid, solid, or a gel. In various embodiments, the described compositions are essentially free of auxins, such as any one or more of indole-3-acetic acid (IAA), indole-3-butryic-acid (IBA), α-naphthaleneacetic acid (NAA), and 2,4-dichlorophenoxyacetic acid (2,4-D).

In some embodiments, the described compositions comprise at least one gibberellin. In such embodiments the at least one gibberellin is one or more of gibberellin A1, gibberellin A4, gibberellin A5, gibberellin A6, gibberellin A7, gibberellic acid ($GA_3$), ent-gibberellane, ent-kaurene, and gibberellin A12. In a particular embodiment, the one or more gibberellin is gibberellic acid, or $GA_3$. In some embodiments, the composition comprises one or more cytokinins that are present in amounts of 0.1 μM to 30 μM or from 1.0 μM to 3.0 μM. In other embodiments, the composition comprises one or more gibberellins or brassinolides that are present either individually or in combination in an amount of 0.1 μM to 30 μM.

In one embodiment, the compositions described herein comprises at least one brassinolides. In such embodiments, the at least one brassinolides is one or more of 2,4-epibrassinolide, 2,8-homo-brassionolide, and 2,4-epi-castasterone.

In certain embodiments the plant media compositions described herein are supplemented with one or more of: vitamins, carbohydrates, buffers, amino acids, complex organic ingredients, salts, and gelling agents. In embodiments where the plant media compositions are supplemented with one or more vitamins, these are in certain embodiments selected from one or more of MS, Gamborgs, Erickson, Chu N6, Schenck & Hildebrandt, Nitsch & Nitsch, Kao & Michayluk Vitamins, Staba Modified Vitamins, Morel & Martin, and Morel & Wettmore vitamin formulations.

In embodiments where the compositions are supplemented with one or more buffers, the one or more buffers possess a pH buffering range of about 5.6 to 5.8 and/or a pKa of about 6.0 to 6.2. In embodiments of the compositions that are supplemented with one or more amino acids, these are in certain instances one or more of alanine, arginine, asparagine, aspartic acid, cysteine, glutamic acid, glutamine, histidine, isoleucine, leucine, lysine, methionine, serine, threonine, tryptophan, tyrosine, and valine.

In embodiments where the compositions are supplemented with one or more complex organic nutrients, such nutrients are one or more of peptone from meat or soy, coconut water, banana powder, tomato powder, pineapple powder, activated charcoal, and casein hydrolysate. Likewise, when gelling agents are included in the compositions, such gelling agent are in certain embodiments selected from one or more of agar, gellan gum, xantham gum, guar gum, gum arabic, agargellan, and carrageenan.

Also provided herein are methods of stimulating, triggering, initiating, and otherwise encouraging the exponential micropropagation in culture of members of the Cannabaceae plant family. Such methods comprise various active steps, including: placing an excised shoot tip onto a cleansing medium, growing the shoot tip on the cleansing medium to yield an elongated shoot, removing the shoot from the cleansing medium, aseptically sectioning the shoot into pieces such that each section comprises at least one node and optionally at least one petiole, placing the section on growth medium, growing the section on the growth medium for at least about 20 days. In such methods, the cleansing medium comprises a basal plant medium comprising indetectable levels of plant growth regulators. Likewise, in such methods, the growth medium comprises: (i) basal plant medium, (ii) one or more cytokinins, and (iii) one or more gibberellins and/or brassinolides, as described above. Remarkably, such methods achieve surprising results wherein the number of nodes and axillary shoots generated by the nodal section is more than if the section were grown on basal plant media alone.

Additional optional steps are also contemplated in certain embodiments. These additional optional steps include: (a) germinating a seedling on basal medium and excising a shoot tip from the germinated seedling, wherein the shoot tip comprises at least a cotyledon and a shoot apical meristem, or (b) excising an ex vitro shoot tip from a grown plant in a vegetative state.

In certain embodiments of the methods described herein, the germinated shoot tip is grown on cleansing medium for at least 20 days or until the shoot tip reaches a length of at least about 1.0 cm, or for at least 30 days. In other embodiments, growing the section on growth medium is performed for at least 20 days or at least 30 days.

In various embodiments, the seedling to which the described methods are applied is a Cannabaceae seedling, a *Cannabis* seedling, a *Humulus* seedling, or a *Celtis* seedling. In a particular embodiment, the seedling is a *Cannabis sativa* L. seedling.

In one embodiment of the described methods, the section further comprises at least one leaf attached to the at least one petiole. The methods described herein contemplate placing the seedling and/or section perpendicularly to the basal medium with the node at least 0.2 cm above the surface of the medium, or placing the seedling and/or section parallel to the basal medium, e.g., layering the seedling or section.

As described above, the present methods achieve remarkable and surprising results not before achieved in the field of Cannabaceae micropropagation. Thus, in certain embodiments, the methods described herein include the ability to subculture the section by repeatedly sectioning and growing on growth media, optionally wherein this step is repeated sixteen (or more) times.

In certain embodiments, sectioning the tissue comprises aseptically clipping the seedling into sections no smaller than about 1 cm in length, and optionally removing any leaves from the section. In other embodiments of the methods described herein, the number of nodes and axillary shoots generated by the section is two to four times more than if the section were grown on basal plant media alone.

This summary is provided to introduce a selection of concepts in a simplified form that are further described below in the Detailed Description. This summary is not intended to identify critical or essential features of the claimed subject matter, nor is it intended to fully limit the scope of the claimed subject matter described more fully hereinbelow.

BRIEF DESCRIPTION OF THE DRAWINGS/FIGURES

For a more precise understanding of the disclosed compositions and methods using the same, reference is made to specific embodiments thereof illustrated in the drawings. The drawings presented herein are not drawn to scale and any reference to dimensions in the drawings or the following description are with reference to specific embodiments. It will be clear to one of skill in the art that variations of these dimensions are possible while still maintaining full functionality for the intended purpose. Such variations are specifically contemplated and incorporated into this disclosure notwithstanding the specific embodiments set forth in the following drawings. Each treatment shown in the figures were grown under the general experimental conditions described in Example 1.

FIG. 1A is a diagram depicting a germinated seedling. FIG. 1B is a diagram depicting a plantlet. These diagrams highlight various developmental aspects of the plantlet discussed herein.

FIG. 2A and FIG. 2B depict representative Golden Kush seedling shoot tips on cleansing medium (DKW) at initiation at day 0 (FIG. 2A), and after 30 days of growth (FIG. 2B). As shown in these Figures, after 30 days of growth in the cleansing medium, apical dominance is reduced compared to seed germination where nodal segments were not elongated, i.e., the only leaves formed are from the cotyledons at the top of the stem.

FIG. 3A and FIG. 3B show representative Golden Kush nodal segments grown on DKWzrg medium at day 0 (FIG. 3A) and after 32 days (FIG. 3B) in which axillary shoot formation is evident. The nodes used to start the culture were obtained from the subculture of seedling shoot tips grown on cleansing medium (DKW without PGRs) shown in FIG. 2B.

FIG. 4A and FIG. 4B depict representative Golden Kush nodes grown in DKW medium at day 0 (FIG. 4A) and after 32 days of growth (FIG. 4B). The nodes used to start the culture were from the subculture of seeding shoot tips grown on cleansing medium (DKW without PGRs), as shown in FIG. 2B. It is noted that no axillary shoots are shown and that the total height of the plantlet is further reduced from the prior subculture shown in FIG. 2B.

FIG. 5A and FIG. 5B are bar graphs of weighted average efficiency (wavgE[%]) of nodes forming axillary shoots from Golden Kush in (FIG. 5A) DKW, and DKWzrg medium and (FIG. 5B) MS and MSzrg medium. An increased average efficiency of axillary shoot formation greater in media containing tZR and $GA_3$ was observed. The depicted error bars are plus and minus one weighted average standard deviation.

FIG. 6A and FIG. 6B show node formation during the PGR induction step. FIG. 6A shows the nodes produced on: Nbasal=DKW, Nc=DKWzr, Ng=DKWg, and Nc+g=DKWzrg with a solid black bar. FIG. 6B shows the net nodes formed from the summation (Nsum) of nodes formed with each component individually, and from the mixture (Nmix).

Figure 15A:
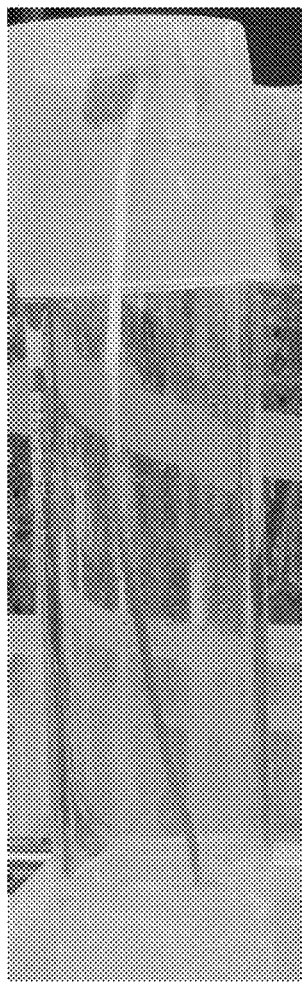
Figure 15B:
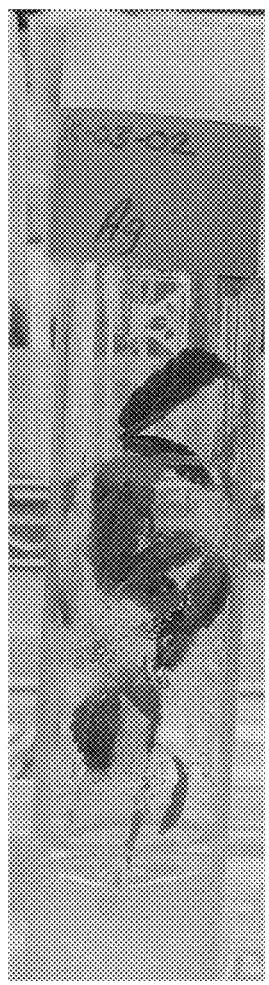
Figure 15C:
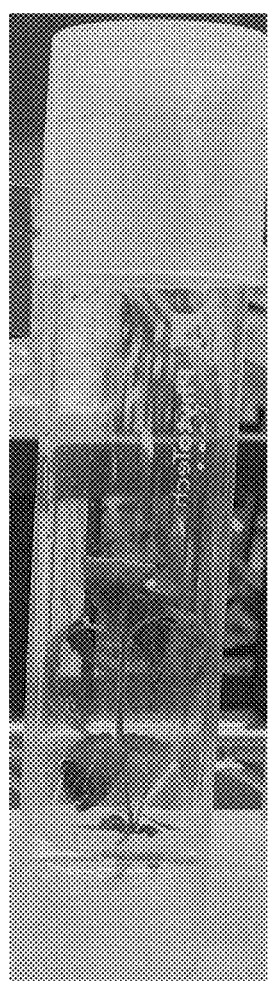

FIG. 15A, FIG. 15B, and FIG. 15C show a representative Golden Kush phenotype nodes denoted as A9 successively grown on DKW medium for each subculture for a germinated seedling after 19 days (FIG. 15A), a seedling shoot tip after 31 days (FIG. 15B), and a node section from the previous seedling shoot tip after 32 days (FIG. 15C). A reduced overall plant height from the seedling phenotype A9, its seedling shoot tip, and node sectioned from its elongated seeding shoot tip, are noted in this experiment.

Figure 16A:
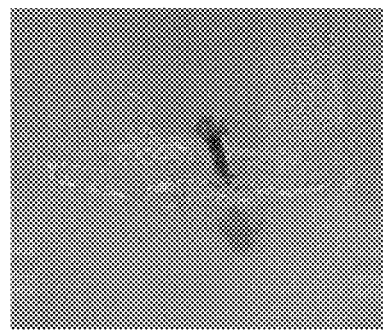
Figure 16B:

FIG. 16A and FIG. 16B show a representative Golden Kush nodal section at day 0 (FIG. 16A) and after 28 days, (FIG. 16B) yielding axillary shoots in DKWnh-brg47 medium following subculture from a single node cut from a grown seeding shoot tip initiated on DKWnh medium.

Figure 17A:
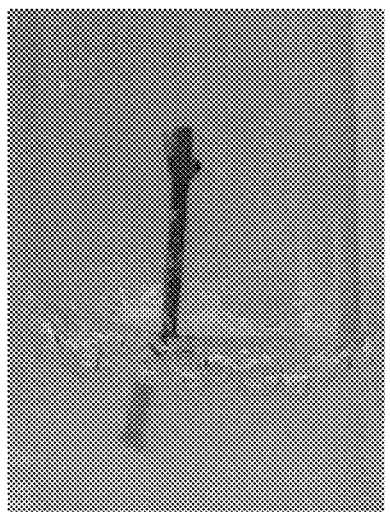
Figure 17B:
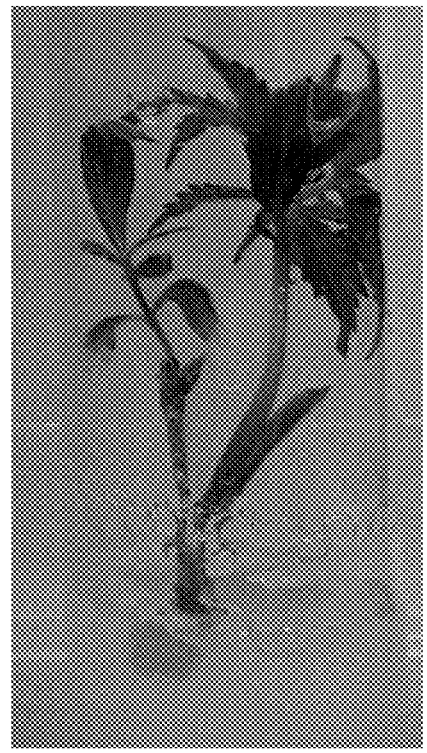

FIG. 17A and FIG. 17B show a representative Golden Kush node at day 0 (FIG. 17A) and after 28 days of growth (FIG. 17B) yielding axillary shoots in DKWnh-mtr28hb medium following subculture from a single node cut from an elongated seeding shoot tip initiated on DKWnh medium.

Figure 18:

FIG. 18 depicts a representative Mandarin Cookies node grown in DKWnhzrg medium after 13 days of culture and showing axillary shoot formation.

Figure 19A:
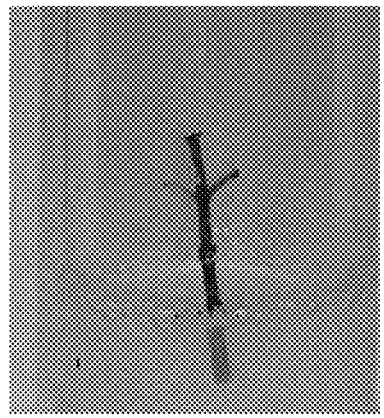
Figure 19B:
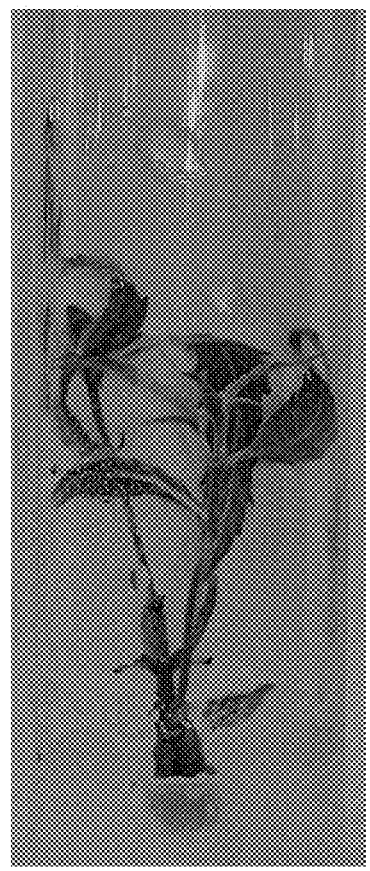

FIG. 19A and FIG. 19B show a representative Golden Kush nodal section at day 0 (FIG. 19A) and after 28 days of growth (FIG. 19B) yielding axillary shoots in DKWnh-mtr28hb medium following subculture from a single node cut from a grown seeding shoot tip initiated on DKWnh medium.

Figure 20A:
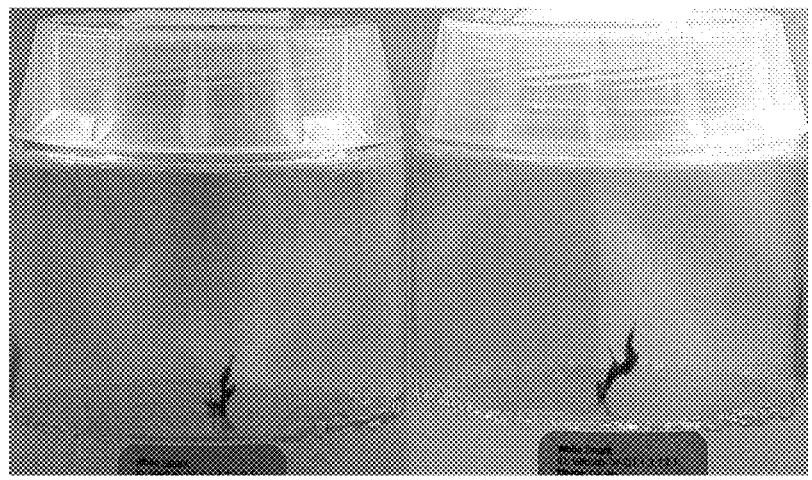
Figure 20B:
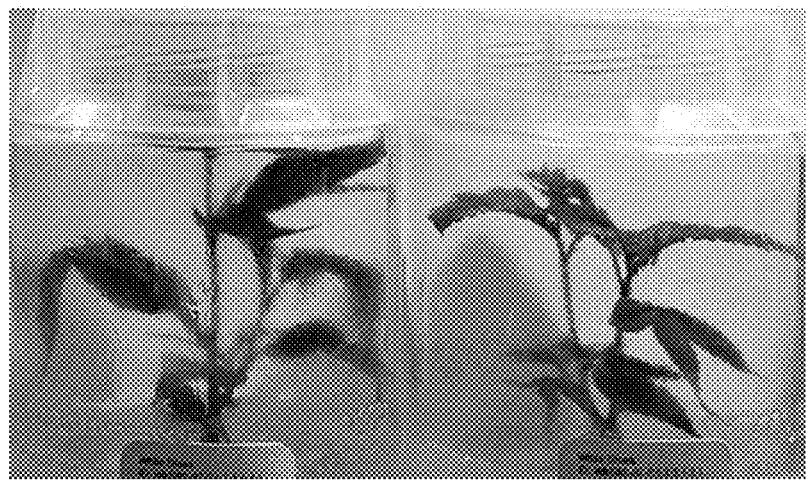

FIG. 20A and FIG. 20B show nodes of White Shark No. 3 at day 0 (FIG. 20A) and after 28 days (FIG. 20B) form axillary shoots after this tissue had been sub-cultured 6 times on DKW1zr1g medium after the initial cleansing step.

Figure 21A:
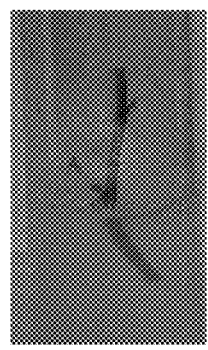
Figure 21B:
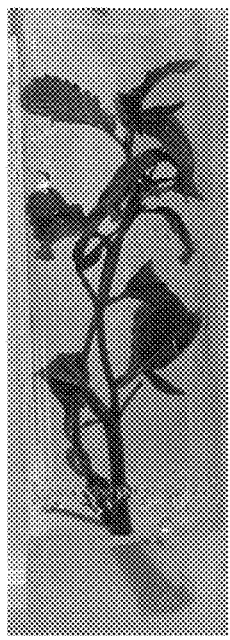

FIG. 21A and FIG. 21B show a representative Golden Kush node at day 0 (FIG. 21A) and after 19 days, (FIG. 21B) yielding axillary shoots in DKW1zr1g medium. This tissue had been previously sub-cultured 16 times on PGR containing media after the initial cleansing step.

DETAILED DESCRIPTION

Definitions

The term "a" or "an" entity as used herein refers to one or more of that entity; for example, "a cell," is understood to represent one or more cells. As such, the terms "a" (or "an"), "one or more," and "at least one" are herein used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "about" or "approximately" refers to a variation of 10% from the indicated values (e.g., 50%, 45%, 40%, etc.), or in case of a range of values, means a 5% to 10% variation from both the lower and upper limits of such ranges. For instance, "about 50%" refers to a range of between 45% and 55%. In a specific embodiment, "about" indicates a 5% variation from the indicated value.

Unless defined otherwise, technical and scientific terms used herein have the same meaning as commonly understood by one of ordinary skill in the art to which this disclosure is related. For example, Plant Propagation by Tissue Culture: Vol. 1 The Background, George, Hall, and De Klerk 3rd ed., 2008 Springer Press; The Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

The term "cytokinin" as used herein means a class of plant growth regulator (PGR) or hormone or phytohormone that promotes cell division and disrupts apical dominance. Cytokinins include adenine-type cytokinins (such as, for example, kinetin, zeatin, and 6-benzylaminopurine) and phenylurea-type cytokinins (such as, for example, diphenylurea and thidiazuron). Cytokinins are generally described as a nucleobase adduct optionally attached to a ribose molecule, and optionally also including a phosphate molecule. Thus, the cytokinin includes at least a nucleobase, optionally attached to a ribose molecule and/or a phosphate molecule.

The term "gibberellin" as used herein contemplates any and all known chemical structures of the gibberellin family including intermediates such as ent-kaurene. Gibberellins are known diterpenoid plant hormones that regulate developmental processes in plants including stem internodal elongation, breaking seed and axillary bud dormancy, flowering, flower development, and the like. The most commonly known gibberellin is gibberellic acid, or $GA_3$. Gibberellins are generally named "$GA_1$" through "$GA_N$" in their order of discovery. There are currently over 130 known gibberellins. (See, Mander Nat. Prod. Rep., 20:49-69, 2003). The known bioactive gibberellins are at least $GA_1$, $GA_3$, $GA_4$, $GA_7$, and $GA_{12}$. Gibberellic acid has the chemical structure (3S,3aS,4S,4aS,7S,9aR,9bR,12S)-7,12-Dihydroxy-3-methyl-6-methylene-2-oxoperhydro-4a,7-methano-9b,3-propenoazuleno [1,2-b]furan-4-carboxylic acid, represented as follows:

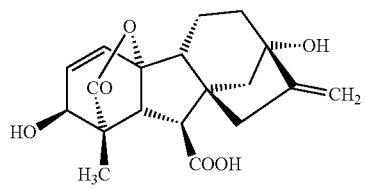

The term "brassinolide" or alternatively "brassinosteroid" or "BR" as used herein contemplates and encompasses all known brassinolides. Brassinolides are a structurally-related family of polyhydroxylated steroidal phytohormones found in plants. Brassinolide itself has the chemical structure: (22R,23R)-2α,3α,22,23-tetrahydroxy-6,7-seco-5α-campestano-6,7-lactone, represented as follows:

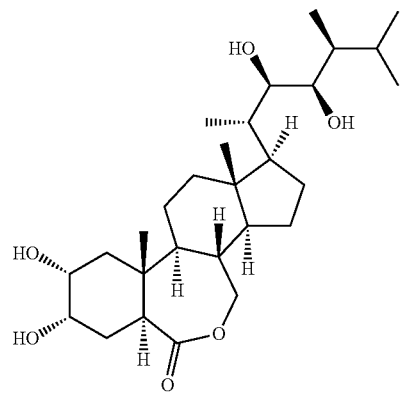

(See, Grove et al., Nature, 281:216-217, 1979). Others in this family of compounds are classified as $C_{27}$, $C_{28}$ or $C_{29}$ based on different alkyl-substitution patterns of the side chains. Over 70 different brassinolide analogs have been reported, isolated from plant tissues of various plant species.

Use of the term "seedling" herein means generated from a plant embryo developing from a seed and comprising a radicle (embryonic root), a hypocotyl (embryonic shoot), and a cotyledon (seed leaves). (See, FIG. 1A).

The term "axillary shoot" as used herein is a shoot or branch that originates from the axil of a leaf or from an axillary bud. (See, FIG. 1B). This term is used interchangeably herein with the term "lateral shoot" and "side shoot." A shoot is a plant part that includes the stem (including appendages), the leaves and lateral bud or flower or flower buds.

The term "axillary bud" as used herein means a plant bud that develops at the axil of a leaf of a plant. This is also sometimes called a lateral bud. Axillary buds develop from nodes which then form axillary shoots. (See, FIG. 1B).

The term "node" as used herein means the point of attachment of a leaf or a twig on a plant stem. (See, FIG. 1B). Nodes contain one or more leaves, as well as axillary buds which can grow into branches.

A "shoot apical meristem" as contemplated herein is a plant organ at the apical end of the embryonic axis which contains pluripotent stem cells that are responsible for the differentiation and growth of the majority of aerial plant organs. (See, FIG. 1A).

Figure 1A:
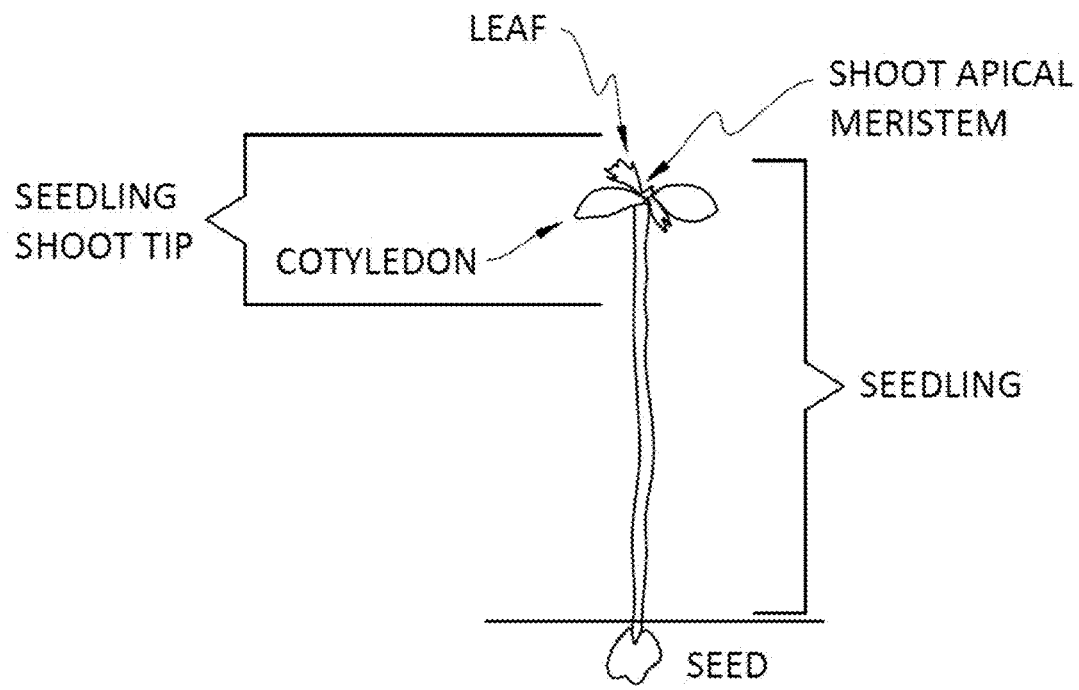
Figure 1B:
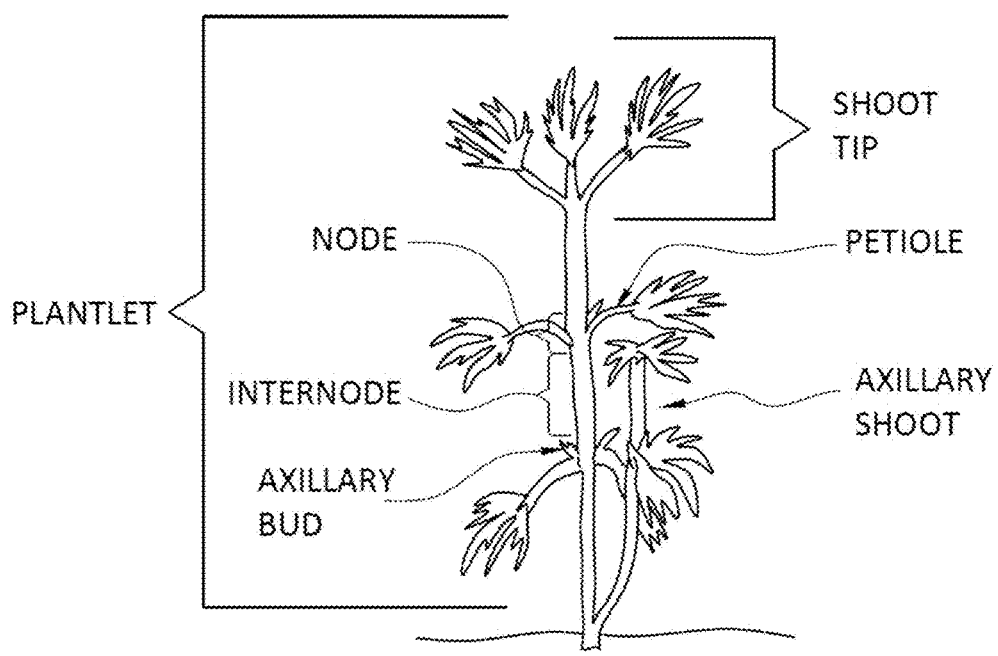

The "cotyledon" is a part of a plant embryo within the seed and is typically defined as an embryonic leaf that first appears in a germinated seed (See, FIG. 1A).

The term "shoot tip" as used herein means the end tip of a stem which includes the shoot apical meristem and includes developing leaves. (See, FIG. 1B).

A "petiole" is a stalk that supports a leaf blade and attaches the leaf bladed to the stem. (See, FIG. 1B).

The term "basal medium" or "base medium," as used herein means mineral salt nutrients (for examples see Tables 1 and 2, below).

The terms "propagation" means the process by which new plants are clonally propagated from various source plant material, such as seeds, cuttings, and the like. Micropropagation often refers to exponential multiplication of stock plant material to produce many progenies and is one method of plant tissue culture. Culturing for propagation of plants can include, for instance, meristem-tip culture, callus culture, suspension culture, embryo culture, and protoplast culture. The term "micropropagation" as used herein generally indicates similar processes executed in vitro.

Micropropagation of *Cannabis*

The Cannabaceae family is a family of flowering, dicotyledonous plants comprised of eleven genera, with the two most well-known being *Humulus* and *Cannabis*. Today this family comprises approximately 117 distinct species and they are of great commercial importance. (See, Zhang et al., *Plant Diversity*, 40:127-137, 2018). A third genus of Cannabaceae, called *Celtis*, comprises by far the largest genus comprising some 100 species. *Cannabis sativa* is one of the most well-known species in this family. Varieties with high tetrahydrocannabinol (THC) concentrations are typically the source of the dried flower used in the production of marijuana, while other varieties, such as hemp (or "industrial hemp," comprising varieties of *Cannabis* typically cultivated for non-drug use), possess low THC concentrations (typically less than 0.3% THC by dry weight) and have been used extensively for fiber and oilseed production for more than 1000 years. (See, Small, "Classification of *Cannabis sativa* L. in Relation to Agricultural, Biotechnological, Medical and Recreational Utilization *Cannabis sativa* and species in particular," *Cannabis sativa* L.—Botany and Biotechnology; Chandra et al., Eds., Springer Nature, 2017). CBD is a secondary metabolite produced in *Cannabis sativa* plants and its commercial production represents a burgeoning industry that has current FDA-approved therapies. However, the commercial production of *Cannabis* has experienced setbacks and challenges due to contamination that have forced recalls of products and lost revenue.

Hops (*Humulus lupulus*) is also in the Cannabaceae family and widely used as an additive in beer manufacturing to provide a sharp taste. Other close phylogenetically-related species in the Rosales order include Peach (*Prunus persica*) and Strawberry (*Fragaria virginiana*) and are agronomically important edible fruits. (Vergara et al., *Mitochondrial DNA Part A: DNA Mapping, Sequencing, and Analysis*, 27:3793-3794, 2015).

Commercial micropropagation through plant tissue culture allows cultivators to start production with tissue that has been decontaminated and/or also disease eradicated. The current state of the art in the commercial micropropagation of *Cannabis* cultivars in vitro is achieved through node culture, or more infrequently via regeneration indirectly from callus. (See, Wang et al., *Pak. J. Bot.*, 41(2):603-608, 2009; Slusarkiewicz-Jarzina et al., *ACTA Biol. Cracov. Series Botanica*, 47/2:145-151, 2005; and Lata et al., *In Vitro Cell. Dev. Biol.-Plant*, 45:12-19, 2009). Node culture is defined as propagation of plants through production of unbranched elongated shoots from cultures of shoot tips or axillary buds. (See, Galan-Avila et al., *Front. Plant Sci.*, 11:645, 2020; and Grulichova et al., Conference: MendelNet 2017—Proceedings of 24th International PhD Students Conference (ISBN 978-80-7509-529-9), At: Mendel University in Brno, Czech Republic, Volume: 24, Nov. 8-9, 2017). Callus resembles organized, lateral root primordial tissue based on gene expression of root cell markers (Sugimoto et al. *Dev. Cell* 18:463-471, 2010). Regeneration of shoots indirectly from callus requires: (1) the induction of callus with plant growth regulator(s), e.g., 3,6-dichloro-o-anisic acid (dicamba), 2,4-dichlorophenoxyacetic acid (2,4-D), and/or thidiazuron (TDZ), and (2) application of growth regulators, i.e., cytokinins with or without auxin, on the callus to produce shoots.

Node culture is well known in the field to be a relatively inefficient process. Many commercially valuable crops are more efficiently produced via shoot culture, the clonal production of plants via enhanced axillary shoot proliferation in the presence of plant growth regulators (PGRs), especially cytokinin, in the culture medium. (See, Kane, "Propagation by Shoot Culture," Plant Tissue Culture, Development and Biotechnology; Trigiano and Gray, Eds; CRC Press, 2011). Micropropagation via shoot culture is a more efficient and ideal method of generating more shoots as compared with node culture and can yield exponential shoot multiplication.

However, for *Cannabis* cultivars there are no known published methods to date that clearly demonstrate sustained PGR-enhanced axillary shoot proliferation. This has been a stumbling block to progress in developing efficient mass production methods in the industry for many years. While a few publications have alleged axillary shoot formation in *Cannabis*, these publications have not demonstrated this achievement over repeated subcultures, a key aspect to maintain micropropagation on a continual basis and is critical for commercial application. (See, Lata et al., *J. Appl. Res. Med. Arora. Plants*, 3:18-26, 2016; Richez-Dumanois et al., *Argonomie*, 6(5):487-495,1986; Wróbel et al., *J. Nat. Fibers*, DOI: 10.1080/15440478.2020.1748160, 2020; and Smýkalová et al., *Plant Cell, Tissue and Organ Culture*, 139:381-394, 2019). Additionally, plant tissues represented photographically from the few published reports on the subject often possess readily identifiable morphogenic abnormalities, and/or short shoots and often cease growth after a few subcultures. Methods involving regeneration of plants indirectly from callus are often not pursued in commercial-scale micropropagation because genomic and epigenetic instability is known to occur when regenerating shoots from callus. (See, Betekhtin et al., *PLoS ONE*, 12(3):e0173537, 2017; and Tanurdzic et al., *PLoS Biol.*, 6(12):e302, 2008).

*Cannabis* plantlet regeneration has also been shown not to occur after inducing callus in two studies. (See, Feeney et al., *In Vitro Cell. Dev. Biol.-Plant*, 39:578-585, 2003; and Monthony et al., bioRxiv, 2020.06.23.167478, 2020). For instance, experiments described in Monthony et al. show that thidiazuron (TDZ) incorporated into Driver and Kuniyuki Walnut (DKW, see Driver et al., *HortScience*, 19:507-509, 1984) nutrient basal medium does not promote *Cannabis* leaf explants to form adventitious shoots following initiation onto media with TDZ as has been asserted by other publications. (See, Wang et al., 2009; Slusarkiewicz- Jarzina et al.; and Lata et al., 2009). TDZ is a cytokinin oxidase inhibitor and is known to affect cytokinin metabolism by limiting the degradation of endogenous cytokinin and thus causing an accumulation of these hormones. (See, Mok et al., *Annu. Rev. Plant Physiol. Plant Mol. Biol.*, 52:89-118, 2001). Applications of high cytokinin concentrations to cultured tissue has been widely reported to induce callus in many plant species since the seminal study of Skoog and Miller, 1957. (See, Skoog et al., *Symp. Soc. Exp. Biol.*, 11:118-30, 1957). It has been known for 25 years that prolonged exposure to TDZ should be avoided due to its potential negative impact on plant growth, including generation of morphogenic abnormalities and hyperhydricity. (See, Lu, Cy, *In Vitro Cell. Dev. Biol.-Plant*, 29:92-96, 1993). These morphogenic abnormalities triggered by prolonged exposure in culture make reliable commercial micropropagation very challenging over repeated subculture.

*Cannabis* sp. are naturally apically dominant, most notably in seedlings (Smýkalová et al., 2019). It has been well established that apical dominance in plants is known to inhibit axillary bud development through auxins. (See, Thimann et al. *Proc. Roy. Soc. B.* 114(789):317-339, 1934). Axillary bud development is necessary to form axillary shoots. More recent evidence suggests the primary repressor of axillary bud development occurs through auxin-dependent biosynthesis of strigolactones. (See, Brewer et al., *Plant Physiol.* 150:482-493, 2009). Strigolactones are carotenoid-derived terpenoids and were recently shown to inhibit axillary shoots as well. (See, Gomez-Roldan et al., *Nature*, 455:189-195, 2008; and Umehara et al., *Nature*, 455:195-201, 2008). More than a hundred other terpenes are known to exist in *Cannabis*. (See, Andre et al., *Front. Plant Sci.*, 7:19, 2016). The apical dominance of *Cannabis* suggests that endogenous auxin and strigolactone concentrations could be high enough to inhibit axillary bud formation, and axillary shot formation. Though the physiology of plants is tightly regulated with regards to the transport of molecules in and out of the plant, the dilution of endogenous hormones, e.g., auxins and strigolactones, based on mass-transfer, i.e., concentration-dependent transport of hormones from plants into cell culture media, was inferred to reduce apical dominance and promote axillary bud development. Provided herein is evidence that this phenomenon is accomplished through placing shoot tips from germinated seedlings or ex vitro plants on a basal medium without plant growth regulators (PGR) for some defined period of time. This was discovered to be a key step in forming axillary shoots in *Cannabis*.

Additionally, it is known that following development of axillary buds, the buds cease growth and become dormant. (See, Shimizu-Sato et al., *Plant Mol. Biol.*, 69:429-435, 2009). Axillary bud dormancy must be broken to allow the outgrowth of axillary shoots, and this is known to occur through the application of cytokinin (Sachs et al., *Amer. J. Bot.*, 54:136-144, 1967), or more recently through gibberellic acid ($GA_3$). (See, Schneider et al., *Front. Plant Sci.*, 10:1296, 2019, doi: 10.3389/fpls.2019.01296). The effect of gibberellic acid ($GA_3$) on the promotion of axillary shoot growth is variable across diverse plant species and in some instances causes axillary shoot growth inhibition. (See, Ni et al., *Plant Cell Physiol.*, 56(8):1655-1666, 2015; Hong-jiu et al., *J. Integ. Agric.*, 19(4):1044-1054, 2020; Sahoo et al., *Plant Cell Reports*, 18:301-307, 1998; Lo et al., *Plant Cell.*, 20:2603-2618, 2008; and Martinez-Bello et al., *J. Exp. Bot.*, 66(19):5897-5910, 2015). The exact mechanism of gibberellin inhibition or promotion of axillary shoot growth is currently unknown. (See, Schneider et al., 2019). This could be related to emerging evidence of the cross-talk between strigolactones and gibberellins. (See, Ito et al., *Plant Physiol.*, 174:1250-1259, 2017; and Zou et al., *J. Plant Physiol.*, 237:72-79, 2019). Further, gibberellins and cytokinins are antagonistic in many developmental processes in plants. (See, Zubo et al., *Plants*, 9:166; doi:10.3390/plants9020166, 2020). The complex interactions observed between strigolactones, gibberellins, and cytokinins may explain the paucity of reports concerning the use of cytokinin-bases, -ribosides, or -riboside 5' monophosphates in combination with gibberellins or brassinolides in *Cannabis* or related species.

As described above, there exists in the field of Cannabaceae micropropagation a stark knowledge gap that precludes development of exponential multiplication of cultivars in a commercially cost-effective manner. While many of the usual pathways for micropropagation have been tried, the results have been very mixed and when hints of success appear they are either not reproducible across multiple subcultures or across other species.

To date there has been no published evidence of the use of a cytokinin, such as trans-zeatin riboside (tZR), in combination with a gibberellin, such as gibberellic acid ($GA_3$), and/or a brassinolide, added to a base plant medium for the purpose of micropropagation of any *Cannabis*, or likely any member of the Cannabaceae family. The three known instances of the combined use of tZR and $GA_3$ to supplement a plant base medium anywhere in the entire field of plant science are found only in the context of regenerating plant tissue from some state, e.g., genetic modification, cryopreservation, and to recover to normal growth. That is to say, such a combination has not been used for production in commercial micropropagation.

For instance, the PGR combination of tZR and $GA_3$ was reported in a regeneration medium that included an auxin (indole-3-acetic acid, IAA) used for the purpose of soybean transformation. (See, Olhoft et al., *Biotech in Ag. and For.*, 61: Transgenic Crops VI, 2007). This instance of the supplementation of basal media with a cytokinin and a gibberellin is quite distinguishable from the presently described compositions and methods because the Olhoft et al. application: (1) included auxin in the medium, which could in other instances counter the ability of tZR and $GA_3$ to form axillary shoots, and (2) had no cleansing step involving the growth of seedlings in media without PGRs prior to exposure to PGRs to reduce apical dominance, which appears to be important in the triggering of formation of axillary shoots in *Cannabis*, (3) shoots generated after growth in this media were not used for further multiplication, rather, they were rooted after exposure to the PGR combination, and (4) the Olhoft et al. medium was used strictly for the regeneration of genetically-modified soybean via *Agrobacterium* transformation.

Two additional past accounts have been published concerning use of tZR and $GA_3$ in the specific context of cryopreservation in a potato regeneration medium. (See, Senula et al., "Cryopreservation and Freeze-Drying Protocols," 4th Ed., *Methods in Molecular Biology*, 2180; and Wolkers et al., Eds. Springer, *Nature*, 2020) and a red raspberry regeneration medium (Ukhatova et al., *In Vitro Cell. Dev. Biol.-Plant*, 53:394-401) post-cryopreservation also with the auxin, IAA, and grown in the dark for 7 days in each method. These instances are also quite distinguishable from the present compositions and methods since: (1) auxins were incorporated in their media, (2) growth was conducted under dark conditions that would prevent positive phototropism in culture, which is necessary for direct shoot growth and obtain shoot height in culture for more nodes, and (3) the end goal of these instances was for recovery of plant tissue that was frozen in liquid nitrogen.

None of these approaches or medium compositions have been reported to be successful in the reliable micropropagation of Cannabaceae plants. Thus, more approaches are needed to address this urgent need in the field. Fortunately, through continued research and development efforts, a specific combination of chemical nutrients, growth regulators, and the like have been formulated herein that markedly and surprisingly supports robust and repeated axillary shoot micropropagation. These compositions and the methods described herein result in upwards of 4-fold increases in axillary shoot generation as compared with other standard basal plant growth media under similar conditions.

Compositions for Axillary Shoot Micropropagation

The compositions described herein therefore begin with a base or standard plant medium. This base is supplemented with: (i) one or more cytokinins, and (ii) one or more gibberellins and/or brassinolides. Each of these components are described below. The amounts of each component vary depending on intended growth conditions specific for each individual species.

The base medium into which the components (i) and (ii), above, are added is defined herein based on: (1) art-recognized medium of historical importance defined by past publications, etc., and (2) select components that when combined create a base medium. Both definitions of base medium are contemplated herein and in general the base medium is not particularly limited other than described below.

Optionally, the base medium also comprises various additives such as vitamins, carbohydrates, buffers, amino acids, complex organic ingredients, salts, and gelling agents.

Base Media: Standard Published Base Media

Plant biology comprises a long and rich history of plant micropropagation efforts that have led to the establishment of art-recognized standard basal media. These media are well known in the field by standard art-recognized terminology and nomenclature. Thus, the base medium incorporated as an initial component into the compositions described herein is not particularly limited.

In some specific instances, it is desirable to eliminate most, if not all, auxins from the compositions described herein. For reasons expressed above, auxins can in some instances inhibit the desired growth of axillary shoots. Thus, in a specific embodiment of the compositions described herein, the compositions herein comprise zero concentration, or no detectable concentration, of auxins. In certain embodiments there is no detectable concentration of auxins present at any time throughout the described methods and compositions.

For instance, the base media useful in the described compositions include, but is not necessarily limited to, Murashige and Skoog (MS) medium (Murashige et al., *Physiol. Plant.*, 15:473-497, 1962), Driver Kuniyaki Walnut (DKW) medium (Driver et al., *HortScience*, 19:507-509, 1984), Lloyd and McCown Woody plant medium (WPM, Lloyd et al., *Proc. Int. Plant Prop. Soc.*, 30:421-427, 1981), Schenk and Hildebrandt medium (Schenk et al., *Can. J. Bot.*, 50:199-204, 1972), Gamborgs B-5 medium (Gamborg et al., *Exp. Cell Res.*, 50:151-158, 1968), BABI medium (Greenway et al., *In Vitro Cell. Dev. Biol.-Plant* 48:403-410, 2012), Chu's N6 medium (Chu et al., *Scientia Sinic.*, 18:659-668, 1975), Quoirin & Lepoivre medium (Quoirin et al., *Acta Hort.*, 78:437-442, 1977), Litvay medium (Litvay et al., Inst. Paper Chemistry, IPC Tech Paper Ser No 115, Appleton, WI.), Hoaglands medium (Hoagland et al., *California Agr. Exp. Sta. Berkley. Circular*, 347, 1950), Anderson medium (Anderson, *Acta Hort.*, 112:13-20, 1980), and Gresshoff & Doy medium (Gresshoff et al., *Z. Pflanzenphysiol.*, 73:132-141, 1974). As noted already, these standard plant base media are well known in the art and described in numerous publications. Generally, these standard media are commercially available from numerous sources throughout the world. In some instances, the base media mentioned herein are commercially available at least from PhytoTech Labs, Inc. of Lenexa, KS, US.

These base media may be altered by known means and in known quantities. For instance, it is well known to utilize, for example, ½× MS media in growth experiments. The nomenclature accepted in the industry is that "½×" means "half strength" or in other words the ½× media comprises only 50% of the ingredients found in the standard, published base plant media so indicated. Likewise, it is quite common to express variations such as "2× MS" and the like, with such expressing having the converse meaning. All such known variations of these base media are contemplated herein and are useful as a beginning base media from which the specific compositions described herein are created.

Certain species of plants of Cannabaceae may grow more robustly on certain described base media above than other base media. Thus, some minor modifications of described protocols may be required to establish a solid performing base medium from which to begin the composition. For example, in the case of *Cannabis*, it is known that at least DKW is a good base medium to include in the compositions described herein.

In one embodiment, the base medium is DKW. In another embodiment, the base medium is MS. In a certain embodiment, the base medium is "NuPS" which is known as containing a base of MS medium plus 2× phosphate, Gamborg's vitamins supplement, 30 g/L sucrose, and 7 g/L agar. Gamborg's vitamins, described in further detail below, is a standard medium supplement used throughout the industry in plant micropropagation and was described by Gamborg et al. in 1968. (See, Gamborg et al., *Exp. Cell Res.*, 50:151-158, 1968). Additional media variations are explained in more detail, below.

Base Media: Basic Components

The base media contemplated herein also is definable based on basic individual components that, when combined in the indicated quantities, create a suitable basal medium. The components listed in Table 1, below, are combined in a manner similar to those present in the known media described above. "EDTA" in Table 1 means ethylenediamine tetraacetic acid. "FeEDDHA" in Table 1 means iron ethylenediamine-N,N'-bis(2-hydroxyphenylacetic) acid.

TABLE 1

| Ion | Minimum Concentration [mM] | Maximum Concentration [mM] |
|---|---|---|
| $NH_4^+$ | 1.00 | 25 |
| $NO_3^-$ | 1.00 | 40 |
| $K^+$ | 1.00 | 40 |
| $Ca^{2+}$ | 0.10 | 10 |
| $Cl^-$ | $1.0 \times 10^{-4}$ | 10 |
| $Mg2+$ | 0.10 | 10 |
| $SO_4^{(2-)}$ | 0.10 | 15 |
| $PO_4^{(3-)}$ | 0.10 | 10 |
| B | $1.0 \times 10^{-3}$ | 1.0 |
| $Na^+$ | $1.0 \times 10^{-2}$ | 10 |
| $Fe^{3+}$ | $1 \times 10^{-3}$ | 1.0 |

TABLE 1-continued

| Ion | Minimum Concentration [mM] | Maximum Concentration [mM] |
| --- | --- | --- |
| EDTA | $1 \times 10^{-3}$ | 1.0 |
| $Mn^{2+}$ | $1 \times 10^{-3}$ | 1.0 |
| $Zn^{2+}$ | $1 \times 10^{-4}$ | 1.0 |
| $Co^{2+}$ | 0 | $1.0 \times 10^{-4}$ |
| $Cu^{2+}$ | $1 \times 10^{-5}$ | $1.0 \times 10^{-3}$ |
| $Mo^{2+}$ | $1 \times 10^{-4}$ | $1.0 \times 10^{-3}$ |
| $I^-$ | 0 | $1.0 \times 10^{-2}$ |
| $Ni^{2+}$ | 0 | $10 \times 10^{-5}$ |

Standard textbooks and treatises or scientific review articles in the fields of botany and plant biology also include descriptions and information enabling one of skill in the art to compose a suitable basal medium from elemental components that are listed in Table 1. This is to say that while standard, well-known, and commercially-available basal plant media are generally suitable in the presently described compositions and methods, contemplated herein are alterations and variations of such published and standard basal media that are also known in the art to be likewise suitable for this purpose.

Further, the base or basal media described herein optionally includes, in some embodiments, various medium additives at various concentrations known in the art. Such additives include, for example, various components such as vitamins, carbohydrates, buffers, amino acids, complex organic ingredients, salts, and gelling agents.

Various publications in the art describe numerous concoctions or combinations of vitamins known to be supportive and generally helpful in the growth and maintenance of various plant species. Such vitamin supplements include, but are not limited to, Murashige and Skoog vitamins (described above in Base Media: Standard Published Base Media), Gamborg's vitamins (described above), Erickson (Eriksson, T., *Physiol. Plant*, 18:976-993, 1965), Chu N6 (described above), Schenck & Hildebrandt (described above), Nitsch and Nitsch (Nitsch et al., *Science*, 163:85-87, 1969), Kao and Michayluk vitamins (Kao et al., *Planta*, 126:105-110, 1975), Staba Modified vitamins (Staba, *Rec. Adv. Phytochem.*, 2:80, 1969), Morel and Martin (Morel et al., Comptes rendus hebdomadaires des seances de l'Academi d'agriculture de France, 41:472-475, 1955), and Morel and Wettmore vitamin (Morel et al., *Am. J. Bot.*, 38:141-143, 1951) formulations. Such well-known formulations are generally commercially available from numerous commercial sources throughout the world.

General concentration ranges of the most common vitamins employed as basal media supplements are as follows:
Myo-Inositol (0 to 1000 mg/L)
para-Aminobenzoic acid (PABA, 0 to 0.5 mg/L)
Calcium pantothenate (0 to 1 mg/L)
Chlorine chloride (0 to 1 mg/L)
Vitamin $B_{12}$ (0 to 0.02 mg/L)
D-biotin (0 to 1 mg/L)
Folic acid (0 to 5 mg/L)
Glycine (0 to 2 mg/L)
Ascorbic acid (0 to 500 mg/L)
Nicotinic acid (0 to 5 mg/L)
Pyridoxine HCl (0 to 1 mg/L)
Thiamine HCl (0 to 10 mg/L)

These concentration ranges are understood to be approximate and encompass deviations about the integers noted. Other chemical components that are contemplated as supplements to the basal media described herein include carbohydrates. In some embodiments the carbohydrate is a simple sugar, such as sucrose. In another embodiment the carbohydrate is glucose. In another embodiment the carbohydrate is fructose. In another embodiment the carbohydrate is sorbitol. In a further embodiment, the carbohydrate is a combination one of more of glucose, sorbitol, and fructose.

Other chemical components that are contemplated as supplements to the basal media described herein include various known salts as set forth in, for example, Table 1.

Other chemical components that are contemplated as supplements to the basal medium described herein include buffering agents. In some embodiments the buffering agent is 2-(N-morpholino)ethanesulfonic Acid (MES). Generally, the function of the additive buffering agent is to maintain a stable buffer pH at approximately 5.6 to 5.8 and/or a pKa of about 6.0 to 6.2. (See, Good et al., *Biochem.* 5(2):467-477, 1966).

Other basal medium additives contemplated herein include various amino acids known to be beneficial to plant growth. Such amino acids include, for example, one or more of alanine, arginine, asparagine, aspartic acid, cysteine, glutamic acid, glutamine, histidine, isoleucine, leucine, lysine, methionine, serine, threonine, tryptophan, tyrosine, and valine, and combinations thereof.

In one embodiment, the additive to the compositions described herein include complex organic ingredients such as peptone from meat or soy, coconut water (0 to about 25% (w/w)), banana powder, tomato powder, pineapple powder, activated charcoal (0 to about 2 g/L), and casein hydrolysate, or combinations thereof.

It is also contemplated herein that in certain embodiments the compositions described herein will be solid or in gel form. The compositions are in one embodiment in powder form. In another embodiment, the composition is sterile, having been sterilized by autoclaving, filtering, or other means known in the art and standard in the art for sterilization of such chemical compositions.

Thus, in one embodiment, the compositions further comprise at least one gelling agent. The gelling agent is, for example, selected from the following: agar, or gellan gum, xantham gum, guar gum, gum arabic, and carrageenan. In one embodiment, the agar is from *Gracilaria* sp. or *Gelidium* sp., or is Carrageenan Gelcarin GP812® (FMC Corporation, Philadelphia, PA, US). In one embodiment the gellan gum is generic, Gelzan (CP Kelco, Atlanta, GA, US), Gelrite, Phytagel (MilliporeSigma, St Louis, MO, US), or agargellan (PhytoTech Labs, Inc., Lenexa, KS, US).

Such additives are also known to be well-tolerated by most plant species and able to be varied by ½x, ⅓x, 2x, 3x and the like. Such variations of these additives are also contemplated herein as being compatible with the herein described compositions and methods.

Cytokinins

The compositions for axillary shoot micropropagation described herein include one or more cytokinins. The cytokinin is present as a base, optionally including a ribose, and optionally also includes a phosphate moiety. Non-limiting examples of such cytokinins are provided in the list below.

In one embodiment, the cytokinin is a nucleobase. In one embodiment, the nucleobase is one or more of: $N^6$-isopentenyladenine (iP, 6-(3,3-dimethylallylaminopurine, CAS No. 2365-40-4), trans-zeatin (tZ, 6-(E)-4-hydroxy-3-methylbut-2-enylaminopurine), meta-topolin (mT, 6-(3-hydroxybenzylaminopurine), dihydrozeatin riboside (DHR, 6-(4-hydroxy-3-methylbutylaminopurine), cis-zeatin (cZ, 6-((Z)-4-hydroxy-3-methylbut-2-enylaminopurine), N6-benzyladenosine (BA, 6-benzylaminopurine), and kinetin (Kin, 6-furfurylaminopurine).

In another embodiment, the cytokinin is a riboside. In one embodiment, the riboside is selected from the non-limiting list of one or more of: $N^6$-isopentenyladenosine (iPR, 6-(3,3-dimethylallylamino)-9-β-D-ribofuranosylpurine), trans-zeatin riboside (tZR, 6-((E)-4-hydroxy-3-methylbut-2-enylamino)-9-β-D-ribofuranosylpurine), meta-topolin riboside (mTR, 6-(3-hydroxybenzylamino)-9-b-D-ribofuranosylpurine), dihydrozeatin riboside (DHZR, 6-(4-hydroxy-3-methylbutylamino)-9-β-D-ribofuranosylpurine), cis-zeatin riboside (cZR, 6-((Z)-4-hydroxy-3-methylbut-2-enylamino)-9-b-D-ribofuranosylpurine), N6-benzyladenosine (BAR, 6-benzylamino-9-β-D-ribofuranosylpurine), and kinetin riboside (KinR, 6-furfurylamino-9-β-D-ribofuranosylpurine).

In a further embodiment, the cytokinin is a riboside-5'-phosphate, which is selected from one or more of the following non-limiting examples: $N^6$-isopentenyladenosine-5'-monophosphate (iPMP, 6-(3,3-dimethylallylamino)-9-b-D-ribofuranosylpurine-5'-monophosphate disodium monohydrate), trans-zeatin riboside-5'-monophosphate (tZMP, 6-((E)-4-hydroxy-3-methylbut-2-enylamino)-9-β-D-ribofuranosylpurine-5'-monophosphate disodium monohydrate), meta-topolin riboside-5'-monophosphate (mTMP, 6-(3-hydroxybenzylamino)-9-β-D-ribofuranosylpurine-5'-monophosphate disodium monohydrate), dihydrozeatin riboside-5'-monophosphate (DZRMP, 6-(4-hydroxy-3-methylbutylamino)-9-β-D-ribofuranosyl purine-5'-monophosphate disodium monohydrate), cis-zeatin riboside-5'-monophosphate (cZMP, 6-((Z)-4-hydroxy-3-methylbut-2-enylamino)-9-β-D-ribofuranosylpurine-5'-monophosphate disodium monohydrate), N6-benzyladenosine-5'-monophosphate (BAMP, 6-benzylamino-9-β-D-ribofuranosylpurine-5'-monophosphate), and kinetin riboside-5'-monophosphate (KMP, 6-furfurylamino-9-β-D-ribofuranosylpurine-5'-monophosphate).

The cytokinin included in the compositions described herein include any one or more combinations of the cytokinins described herein. In one particular embodiment, the cytokinin is tZR. In another embodiment, the cytokinin is iPR. In a further embodiment, the cytokinin is a mixture of tZR and iPR.

The amount of cytokinin included in the composition will vary depending on the exact species of Cannabaceae, and sometimes the phenotype being grown and other factors. In certain embodiments of the described compositions, the one or more cytokinins are present in amounts of about 0.1 μM to about 30 μM or from about 1.0 μM to about 3.0 μM. That is, the cytokinin is present at anywhere from about 0.1 μM to about 30 μM. In a particular embodiment, the cytokinin total concentration present in the composition is from about 1.0 μM to about 3.0 μM. In certain embodiments, the cytokinin total concentration in the compositions described herein are from about 0.1 μM to 30 μM, about 0.5 μM to 25 μM, about 1.0 μM to 20 μM, about 1.5 μM to 15 μM, about 2.0 μM to 10 μM, about 2.5 μM to 5 μM, about 0.1 μM to 6 μM, about 0.2 μM to 5 μM, about 0.3 μM to 4.0 μM, about 0.4 μM to 3.0 μM, or from about 0.5 μM to about 2.0 μM.

More particularly, in a particular embodiment, the cytokinin total concentration is about 0.5 mg/L or about 2 mg/L (about 1.4 μM to about 5.6 μM). In one embodiment, the cytokinin is tZR, which is present at from 0.5 to 2 mg/L (about 1.4 μM to about 5.6 μM) in the composition.

Gibberellins and Brassinolides

The compositions described herein comprise not only basal plant media, but also one or more cytokinins along with one or more gibberellins or brassinolides. In one embodiment, the composition comprises at least one gibberellin. In another embodiment, the composition comprises at least one gibberellin and at least one brassinolide. In another embodiment, the composition comprises at least one brassinolide.

The gibberellins, as used herein, and as noted above, contemplated to be suitable for use in the described compositions includes any one or more of the following non-limiting examples: gibberellin $A_1$, gibberellin $A_4$, gibberellin $A_5$, gibberellin $A_6$, gibberellin $A_7$, gibberellic acid, ent-gibberellane, ent-kaurene, and gibberellin A12. In one embodiment, the composition comprises both gibberellin $A_4$ and gibberellin $A_7$ which are commonly commercially available together as a powder. In one embodiment, the gibberellin is specifically and only gibberellic acid, or gibberellin $A_3$.

The compositions described herein are contemplated also optionally include one or more brassinolides. The compositions comprise either a brassinolide or a gibberellin, but in some embodiments the composition includes species of both genera of compounds.

Thus, in certain embodiments, the composition described herein includes at least one brassinolide selected from one or more of: 2,4-epi-brassinolide, 2,8-homo-brassionolide, and 2,4-epi-castasterone, for example. In one embodiment, the composition comprises at least one brassinolide, wherein in certain embodiments that brassinolide is 2,4-epi-brassinolide.

The gibberellins and/or brassinolides present in the described compositions are present at various concentrations and at various ratios with respect to cytokinin. For example, it is contemplated herein that the one or more gibberellins and/or brassinolides are present in an amount of about 0.1 μM to about 10 μM in the described compositions. Alternatively, in some embodiments, the gibberellins and/or brassinolides are present in an amount of about 0.1 μM to 9 μM, about 0.3 μM to 8 μM, about 0.5 μM to 7 μM, about 1.0 μM to 7.5 μM, about 1.5 μM to 6.0 μM, about 5.0 μM to 4.0 μM, about 0.25 μM to 7.0 μM, about 0.5 μM to 7.0 μM, about 0.75 μM to 7.0 μM, about 5 μM to 7 μM, about 6.0 μM to 7.0 μM, about 5.0 μM to 10 μM, or from about 1.0 μM to about 7.0 μM. In a specific embodiment, the gibberellins and/or brassinolides are present in an amount of about 6.8 μM.

In another embodiment, the one or more gibberellins and/or brassinolides are present in an amount of about 0.5 mg/L to about 2.0 mg/L (about 0.72 μM to about 5.8 μM) of the composition. In one particular embodiment the compositions comprise at least gibberellic acid or 2,4-epi-brassinolide at a concentration of about 0.25 mg/L to about 2.0 mg/L (about 0.72 μM to about 5.8 μM) of the composition.

Furthermore, various ratios of cytokinin concentration to gibberellin and/or brassinolide concentrations are contemplated herein. When the composition comprises both a cytokinin and a gibberellin, the ratio of concentrations between the two components, in one embodiment, is 1:1. In such an embodiment, the composition comprises at least tZR and gibberellic acid at approximately a 1:1 ratio. In other embodiments, the ratio between cytokinin:(gibberellin and/or brassinolide) is 0.1:1, 0.2:1, 0.3:1, 0.4:1, 0.5:1, 0.6:1, 0.7:1, 0.8:1, 0.9:1, 1:0.1, 1:0.2, 1:0.3, 1:0.4, 1:0.5, 1:0.6, 1:0.7, 1:0.8, or 1:0.9. In some embodiments, the ratio of a) cytokinin to b) gibberellin and/or brassinolide is between 50:1 and 1:50. In other embodiments, said ratio is from 40:1, 30:1, 20:1, 10:1, 1:1, 1:10, 1:20, 1:30, 1:40, and 1:50.

Methods of Micropropagation

Provided herein are methods of propagating plants in the Cannabaceae family. It is contemplated and expected herein that the compositions and methods provided herein may be useful in the propagation of other plant species, not just including those of the Cannabaceae family. In one embodiment, the plant species able to be propagated by the described methods herein is *Cannabis*. In another embodiment the species is *Humulus*. In one embodiment the plant is hemp. Any member of the Cannabaceae family related to *Cannabis* will likely greatly benefit from the methods described herein due to similarities in physiological requirements for growth and propagation.

The methods described herein are necessarily a multi-step process. The starting materials for the methods are varied. Likewise, the species and family of the plant to be propagated is variable. However, in one embodiment the plant species is *Cannabis*.

In one embodiment the beginning material for the method described herein is an excised shoot tip. The shoot tip in one embodiment is excised from a grown, optionally vegetative plant. In another embodiment, the shoot tip is from a germinated seedling.

The various method steps include at least the following: placing an excised shoot tip onto a cleansing medium, growing the shoot tip on the cleansing medium to yield an elongated shoot, removing the shoot from the cleansing medium, sectioning aseptically the shoot into sections such that each section comprises at least one node and optionally at least one petiole, placing the section on growth medium, and growing the section on the growth medium for at least about 20 days. In such methods the cleansing medium comprises a basal plant media comprising indetectable levels of plant growth regulators and the growth medium comprises: (i) basal plant medium, (ii) one or more cytokinins, and (iii) one or more gibberellins and/or brassinolides. Thus, the growth medium is identical and synonymous with the compositions described hereinabove.

In such methods the section is performed by use of a scalpel, and in one embodiment the section is entirely performed aseptically to avoid any possibility of cross-contamination with infectious agents. Such aseptic procedures and equipment are known in the art and described in the examples section, below. (See, Example 1).

Thus, the methods described herein generally require two basic steps. First is the growth on cleaning medium to rid the plantlet of any contaminating chemicals, PGRs, and the like prior to stimulation to produce axillary shoots. It has been found in experiments that this step is helpful. (See, e.g., Example 11). However, it is contemplated that at least in some instances the cleansing step may not be absolutely necessary to achieve multiplication of axillary shoots in this plant family.

The multiplication generated in the indicated plant family and species ranges anywhere from 2- to 4-fold the number of nodes and axillary shoots generated as compared with growth on basal plant media alone containing no added cytokinin or gibberellins or brassinolides. In some embodiments, the multiplication of nodes and axillary shoots is as high as about 5-fold, about 6-fold, about 7-fold, about 8-fold, or even about 10-fold.

Thus, in one embodiment, the method also includes the steps for germinating a seedling on basal media, and excising a shoot tip from the germinated seedling, wherein the shoot tip comprises at least a cotyledon and a shoot apical meristem. However, this step is considered optional since it has been shown (below) that the single step of excising an ex vitro shoot tip from a grown plant in a vegetative state is also suitable and generates similar remarkable results.

In general, the shoot tip is grown on the cleansing medium for about 20 days. However, in another embodiment, the shoot tip is grown on the cleansing medium for as many as about 30 days. The shoot tip is grown on cleansing medium in certain embodiments for as many as about 15, 16, 17, 18, 19, 20, 21, 22, 23, 24, 25, 26, 27, 28, 29, 30, 31, 32, 33, 34, 35, 36, 37, 38, 39, or even about 40 days. In general, the shoot tip is to be grown on the cleansing medium for about 15 days to about 35 days for optimal results in certain species of plant.

In general, the section is grown on the growth medium, i.e., the compositions described herein, for about 20 days. However, in another embodiment, the section is grown on the growth medium for as many as about 30 days. The section is grown on growth medium in certain embodiments for as many as about 15, 16, 17, 18, 19, 20, 21, 22, 23, 24, 25, 26, 27, 28, 29, 30, 31, 32, 33, 34, 35, 36, 37, 38, 39, or even about 40 days. In general, the section is to be grown on the growth medium for about 15 to 35 days for optimal results in certain species of plant.

Contemplated within the methods described herein is the ability to subculture the yielded plants. In one embodiment, the methods enable subculturing as many as about 2, 3, 4, 5, 6, 7, 8, 9, or even about 10 times. In one particular embodiment, the method allows for at least four subcultures to be achieved reproducibly. In one embodiment of subculturing the species of plant is *Cannabis*.

Other details of the contemplated methods described herein are described in the Examples provided below.

Further modifications and alternative embodiments of various aspects of the methods and compositions described herein will be apparent to those skilled in the art in view of this description. Accordingly, this description is to be construed as illustrative only and is for the purpose of teaching those skilled in the art the general manner of carrying out the disclosed methods and systems. It is to be understood that the forms of the disclosed methods and systems shown and described herein are to be taken as examples of embodiments. Elements and materials may be substituted for those illustrated and described herein, parts and processes may be reversed, and certain features of the disclosed methods and systems are capable of being utilized independently, all as would be apparent to one skilled in the art after having the benefit of this description of the disclosed methods and systems. Changes may be made in the elements described herein without departing from the spirit and scope of the disclosed methods and systems as described in the following claims.

All of the references cited above, as well as all references cited herein, are incorporated herein by reference in their entireties. The following examples are offered by way of illustration and not by way of limitation.

EXAMPLES

Example 1: Plant Material and Germination

Materials: if not otherwise indicated, all reagents were obtained from PhytoTech Labs, Inc., Lenexa, KS, US. 6-(γ,γ-dimethylallylamino)purine riboside (iPR) was obtained from Cayman Chemical, Ann Arbor, MI, US. Dihydrozeatin riboside (dHZR) was obtained from Muse Chem, Fairfield, NJ, US. Benzyladenine riboside (BAR) and 28 Homo brassinolide were obtained from Carbosynth, Berkshire, UK. meta-Topolin riboside (mTR) was obtained from AmBeed, Arlington Heights, IL, US. Golden Kush hemp seeds were obtained from Phytonyx, Ashland, OR, US. Sundae Cake, Mandarin Cookies No. 1, and White Shark No. 3 were from NuLeaf Sparks Cultivation, Inc., Las Vegas, NV, US.

Golden Kush Lighting: 48 inch, two T8 fluorescent bulbs, 64 total watts, were from Lithonia Lighting, Conyers, GA, US, and were mounted about 10 to 15 inches above the top of the test tubes. The light intensity was approximately 50 $\mu mol/m^2 s^1$.

Sundae Cake, Mandarin Cookies No. 1, and White Shark No. 3 Lighting: RAZR2 LED arrays were obtained from Fluence Bioengineering, Austin, TX, US and were mounted approximately 6 to 8 inches above the containers. The light intensity was approximately 25 to 30 $\mu mol/m^2 s^1$ for Sundae Cake, and 40 to 50 $\mu mol/m^2 s^1$ for Mandarin Cookies No. 1, and White Shark No. 3.

The photoperiod for both lighting regimes was about 16 hours on and about 8 hours off. All tissue culture was performed at normal atmosphere at about 22° C. to about 26° C. with approximately 35% to 50% relative humidity in growth rooms. All growth occurred in capped culture tubes to maintain sterile environments.

Disinfection: seeds were disinfected in a 10% (v/v) aqueous solution of CHLOROX® bleach (0.8% sodium hypochlorite solution) also containing 0.12% (v/v) TWEEN® 20 for 15 minutes. The seeds were then washed five times with autoclaved and distilled water. Seeds were then placed on 20 mL of gelled germination medium in 25 mm×150 mm culture tubes. For germination, media including either ½× MS (50% MS) basal medium, MS basal medium, DKW basal medium, or DKWnh basal medium was used.

½× MS basal medium was half-strength in MS macro- and micro-nutrients plus Gamborg's vitamins, sucrose as a carbon source, and agar as a gelling agent. The pH was adjusted to approximately 5.6 to 5.8 before autoclaving (for further details of the medium composition, see Table 2, below).

MS basal medium was full-strength in MS macro- and micro-nutrients plus Gamborg's vitamins, sucrose as a carbon source, and agar as a gelling agent. The pH was adjusted to approximately 5.6 to 5.8 before autoclaving (for further details of the medium composition, see Table 2 below).

DKW basal medium was full-strength DKW macro- and micronutrients plus Gamborg's vitamins, sucrose as a carbon source, and agar as a gelling agent. The pH was adjusted to approximately 5.6 to 5.8 before autoclaving (for further details of the medium composition, see Table 2 below).

DKWnh basal medium was a modified DKW basal medium plus Gamborg's vitamins, sucrose as a carbon source, and agar as a gelling agent. The pH was adjusted to approximately 5.6 to 5.8 before autoclaving (for further details of the medium composition, see Table 2 below).

Excision: all plant tissue (nodes on shoot-tips) was excised or cut aseptically at ambient temperature in an ISO 5 (class 100) laminar flow hood operating at a flow rate of about 70 to 110 feet per minute using a sterilized scalpel. Excised plant tissue was then transferred into 25 mm×150 mm glass or polycarbonate culture tubes containing gelled media using sterile forceps or tweezers. Each tube was covered individually with a polypropylene cap.

Germination: seeds were germinated under the growth and lighting conditions described above. In general, 80% of the seeds germinated on ½× MS and MS and 60% on DKW in 10 to 35 days. Germination on DKW was generally slower with a lower germination efficiency

TABLE 2

| Media Component Concentrations [mg/L] | | | | | | | |
|---|---|---|---|---|---|---|---|
| Component | 1/2XMS | MS | DKW | 1/2XMSzrg | MSzrg | DKWzrg | DKWiprg |
| Macroelements | | | | | | | |
| $KNO_3$ | 950 | 1900 | 0 | 950 | 1900 | 0 | 0 |
| $NH_4NO_3$ | 825 | 1650 | 1416 | 825 | 1650 | 1416 | 1416 |
| $Ca(NO_3)_2$ anhydrous | 0 | 0 | 1367 | 0 | 0 | 1367 | 1367 |
| $CaCl_2$ anhydrous | 166.1 | 332.2 | 112.5 | 166.1 | 332.2 | 112.5 | 112.5 |
| $MgSO_4$ anhydrous | 90.35 | 180.7 | 361.49 | 90.35 | 180.7 | 361.49 | 361.49 |
| $KH_2PO_4$ | 85 | 170 | 265 | 85 | 170 | 265 | 265 |
| $K_2SO_4$ | 0 | 0 | 1559 | 0 | 0 | 1559 | 1559 |
| Microelements | | | | | | | |
| $H_3BO_3$ | 3.1 | 6.2 | 4.8 | 3.1 | 6.2 | 4.8 | 4.8 |
| $CuSO_4 \cdot 5H_2O$ | 0.0125 | 0.025 | 0.25 | 0.0125 | 0.025 | 0.25 | 0.25 |
| $CoCl_2 \cdot 6H_2O$ | 0.0125 | 0.025 | 0 | 0.0125 | 0.025 | 0 | 0 |
| $Na_2EDTA \cdot 2H_2O$ | 18.63 | 37.26 | 45.4 | 18.63 | 37.26 | 45.4 | 45.4 |
| $FeSO_4 \cdot 7H_2O$ | 13.9 | 27.8 | 33.8 | 13.9 | 27.8 | 33.8 | 33.8 |
| $MnSO_4 \cdot H_2O$ | 8.45 | 16.9 | 33.5 | 8.45 | 16.9 | 33.5 | 33.5 |
| $Na_2MoO_4 \cdot 2H_2O$ | 0.125 | 0.25 | 0.39 | 0.125 | 0.25 | 0.39 | 0.39 |
| $NiSO_4 \cdot 6H_2O$ | 0 | 0 | 0.005 | 0 | 0 | 0.005 | 0.005 |
| KI | 0.415 | 0.83 | 0 | 0.415 | 0.83 | 0 | 0 |
| $ZnSO_4 \cdot 7H_2O$ | 4.3 | 8.6 | 0 | 4.3 | 8.6 | 0 | 0 |
| $ZnNO_3 \cdot 6H_2O$ | 0 | 0 | 17 | 0 | 0 | 17 | 17 |
| Vitamins | | | | | | | |
| myo-Inositol | 100 | 100 | 100 | 100 | 100 | 100 | 100 |
| Nicotinic Acid | 1 | 1 | 1 | 1 | 1 | 1 | 1 |
| Pyridoxine HCl | 1 | 1 | 1 | 1 | 1 | 1 | 1 |
| Thiamine HCl | 10 | 10 | 10 | 10 | 10 | 10 | 10 |

TABLE 2-continued

| Media Component Concentrations [mg/L] | | | | | | | |
|---|---|---|---|---|---|---|---|
| Plant Growth Regulators | | | | | | | |
| trans-Zeatin riboside | 0 | 0 | 0 | 0.5 | 0.5 | 0.5 | 0 |
| 6-(γ,γ-Dimethyl-allylamino) purine riboside | 0 | 0 | 0 | 0 | 0 | 0 | 0.5 |
| Gibberellic acid | 0 | 0 | 0 | 0.5 | 0.5 | 0.5 | 0.5 |
| Carbohydrates | | | | | | | |
| Sucrose | 30 | 30 | 30 | 30 | 30 | 30 | 30 |
| Gelling agents | | | | | | | |
| Agar | 7 | 7 | 7 | 7 | 7 | 7 | 7 |

| Component | DKWdhzrg | DKWtrepi | DKWtzg | DKW2zr2g | DKWnh | DKWnh-brg47 |
|---|---|---|---|---|---|---|
| Macroelements | | | | | | |
| KNO$_3$ | 0 | 0 | 0 | 0 | 600 | 600 |
| NH$_4$NO$_3$ | 1416 | 1416 | 1416 | 1416 | 800 | 800 |
| Ca(NO$_3$)$_2$ anhydrous | 1367 | 1367 | 1367 | 1367 | 1367 | 1367 |
| CaCl$_2$ anhydrous | 112.5 | 112.5 | 112.5 | 112.5 | 112.5 | 112.5 |
| MgSO$_4$ anhydrous | 361.49 | 361.49 | 361.49 | 361.49 | 361.5 | 361.49 |
| KH$_2$PO$_4$ | 265 | 265 | 265 | 265 | 265 | 265 |
| K$_2$SO$_4$ | 1559 | 1559 | 1559 | 1559 | 1300 | 1300 |
| Microelements | | | | | | |
| H$_3$BO$_3$ | 4.8 | 4.8 | 4.8 | 4.8 | 4.8 | 4.8 |
| CuSO$_4$•5H$_2$O | 0.25 | 0.25 | 0.25 | 0.25 | 0.25 | 0.25 |
| Na$_2$EDTA•2H$_2$O | 45.4 | 45.4 | 45.4 | 45.4 | 45.4 | 45.4 |
| FeSO$_4$•7H$_2$O | 33.8 | 33.8 | 33.8 | 33.8 | 33.8 | 33.8 |
| MnSO$_4$•H$_2$O | 33.5 | 33.5 | 33.5 | 33.5 | 33.5 | 33.5 |
| Na$_2$MoO$_4$•2H$_2$O | 0.39 | 0.39 | 0.39 | 0.39 | 0.39 | 0.39 |
| NiSO$_4$•6H$_2$O | 0.005 | 0.005 | 0.005 | 0.005 | 0 | 0 |
| ZnNO$_3$•6H$_2$O | 17 | 17 | 17 | 17 | 17 | 17 |
| Vitamins | | | | | | |
| myo-Inositol | 100 | 100 | 100 | 100 | 100 | 100 |
| Nicotinic Acid | 1 | 1 | 1 | 1 | 1 | 1 |
| Pyridoxine HCl | 1 | 1 | 1 | 1 | 1 | 1 |
| Thiamine HCl | 10 | 10 | 10 | 10 | 10 | 10 |
| Plant Growth Regulators | | | | | | |
| trans-Zeatin | 0 | 0 | 0.33 | 0 | 0 | 0 |
| trans-Zeatin riboside | 0 | 0.5 | 0 | 2 | 0 | 0 |
| dihydrozeatin riboside | 0.5 | 0 | 0 | 0 | 0 | 0 |
| Benzyladenine riboside | 0 | 0 | 0 | 0 | 0 | 0.5 |
| Gibberellic acid (GA$_3$) | 0.5 | 0 | 0.5 | 2 | 0 | 0 |
| Gibberellic acid (GA$_4$ + GA$_7$) | 0 | 0 | 0 | 0 | 0 | 0.7 |
| 2,4 epi-brassinolide | 0 | 0.34 | 0 | 0 | 0 | 0 |
| Carbohydrates | | | | | | |
| Sucrose | 30 | 30 | 30 | 30 | 30 | 30 |
| Gelling agents | | | | | | |
| Agar | 7 | 7 | 7 | 7 | 7 | 7 |

| Component | DKWnhzrg | DKWnh-mtr28hb | QL | QLzrg | DKWlzrlg |
|---|---|---|---|---|---|
| Macroelements | | | | | |
| KNO$_3$ | 600 | 600 | 1800 | 1800 | 0 |
| NH$_4$NO$_3$ | 800 | 800 | 400 | 400 | 1416 |
| Ca(NO$_3$)$_2$ anhydrous | 1367 | 1367 | 834 | 834 | 1367 |
| CaCl$_2$ anhydrous | 112.5 | 112.5 | 0 | 0 | 112.5 |

TABLE 2-continued

| Media Component Concentrations [mg/L] | | | | | |
|---|---|---|---|---|---|
| MgSO$_4$ anhydrous | 361.5 | 361.5 | 175.8 | 175.8 | 361.5 |
| KH$_2$PO$_4$ | 265 | 265 | 270 | 270 | 265 |
| K$_2$SO$_4$ | 1300 | 1300 | 0 | 0 | 1559 |
| Microelements | | | | | |
| H$_3$BO$_3$ | 4.8 | 4.8 | 6.2 | 6.2 | 4.8 |
| CoCl$_2$•6H$_2$O | 0 | 0 | 0.025 | 0.025 | 0.25 |
| CuSO$_4$•5H$_2$O | 0.25 | 0.25 | 0.025 | 0.025 | 0 |
| Na$_2$EDTA•2H$_2$O | 45.4 | 45.4 | 37.3 | 37.3 | 45.4 |
| FeSO$_4$•7H$_2$O | 33.8 | 33.8 | 27.8 | 27.8 | 33.8 |
| MnSO$_4$•H$_2$O | 33.5 | 33.5 | 0.76 | 0.76 | 33.5 |
| Na$_2$MoO$_4$•2H$_2$O | 0.39 | 0.39 | 0.25 | 0.25 | 0.39 |
| NiSO$_4$•6H$_2$O | 0 | 0 | 0 | 0 | 0.005 |
| KI | 0 | 0 | 0.08 | 0.08 | 0 |
| ZnNO$_3$•6H$_2$O | 17 | 17 | 0 | 0 | 0 |
| ZnSO$_4$•7H$_2$O | 0 | 0 | 8.6 | 8.6 | 17 |
| Vitamins | | | | | |
| myo-Inositol | 100 | 100 | 100 | 100 | 100 |
| Nicotinic Acid | 1 | 1 | 1 | 1 | 1 |
| Pyridoxine HCl | 1 | 1 | 1 | 1 | 1 |
| Thiamine HCl | 10 | 10 | 10 | 10 | 10 |
| Plant Growth Regulators | | | | | |
| trans-Zeatin riboside | 0.5 | 0 | 0 | 0.5 | 1 |
| Gibberellic acid (GA$_3$) | 0.5 | 0 | 0 | 0.5 | 1 |
| meta-Topolin riboside | 0 | 0.55 | 0 | 0 | 0 |
| 28 homobrassinolide | 0 | 0.69 | 0 | 0 | 0 |
| Carbohydrates | | | | | |
| Sucrose | 30 | 30 | 30 | 30 | 30 |
| Gelling agents | | | | | |
| Agar | 7 | 7 | 7 | 7 | 7 |

Example 2: Culture Initiation of Seedling Shoot Tips

In this example germinated seedling shoot tips of Golden Kush were placed on a basal medium without PGRs to reduce apical dominance and to aid in promoting axillary bud formation.

Golden Kush seedlings were grown approximately 10 cm to 13 cm in height (this height was achieved as early as 14 days under standard growth conditions detailed in Example 1) and the shoot tips were cut to a size of 1.0 cm in length per piece of tissue that included the cotyledons and shoot apical meristem. Each tissue was transferred to 20 mL of fresh ½×MS, MS, or DKW gelled medium in a sterile culture tube in a laminar flow hood. The shoot tip was placed vertically into the medium with the cotyledon and shoot apical meristem approximately 0.2 cm above the medium surface. The seedling shoot tips were then placed in the growth room at the conditions described in Example 1 for 30 days.

Typically, each shoot tip formed 2 to 3 acceptable nodes that included one shoot apical meristem which was selected for further subculture. Acceptable nodes were those tissues that were at least about 1.0 cm in length and that included at least one node. Occasionally, more than one node with undeveloped leaves was present in the approx. 1.0 cm long piece of tissue. These acceptable nodes were recorded at subculture.

Figure 2A:
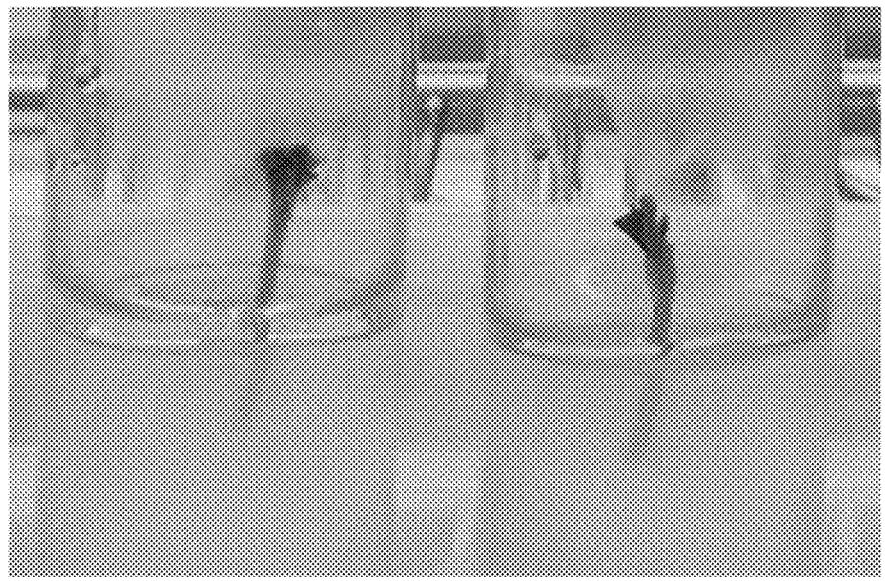
Figure 2B:

Results are shown in FIG. 2. This example shows the importance of the use of cleansing medium to the formation of axillary shoots (see Example 3, below), as initiation of seedling shoot tips directly on plant growth media do not form axillary shoots. For instance, as shown in FIG. 2A (without cleaning), seedling shoot tips at day 0 and FIG. 2B (with cleansing), seedling shoot tips after 30 days of growth. The apical dominance has been reduced as growth height was reduced compared to growth during germination over a similar period of time of growth, and internodes formed.

Example 3: Axillary Shoot Induction

This example focuses on determining whether PGRs in media would promote axillary shoot formation.

Golden Kush nodes that were developed during the growth of the seedling shoot tips for 30 days in Example 2 were cut under aseptic conditions in a laminar flow hood to a length of at least 1.0 cm and the leaves removed by cutting the petiole halfway between the leaf-blade and the stem. Each node was placed on 20 mL of a gelled axillary shoot formation medium in a sterile test tube. This medium was either ½×MSzrg, MSzrg, or DKWzrg media. Basal media including ½×MS, MS, or DKW were also used as negative controls.

The ½×MSzrg medium was half-strength in MS macro- and micro-nutrients plus Gamborg's vitamins, sucrose as a carbon source, trans-zeatin riboside as a cytokinin plant growth regulator, gibberellic acid as a gibberellin plant regulator, and agar as a gelling agent. The pH was adjusted to 5.6 to 5.8 before autoclaving (for further details of the medium composition see Table 2).

The MSzrg medium was full-strength in MS macro- and micro-nutrients plus Gamborg's vitamins, sucrose as a carbon source, trans-zeatin riboside as a cytokinin plant growth regulator, gibberellic acid as a gibberellin plant regulator, and agar as a gelling agent. The pH was adjusted to 5.6 to 5.8 before autoclaving (for further details of the medium composition see Table 2).

The DKWzrg medium was full strength DKW macro- and micro-nutrients plus Gamborg's vitamins, sucrose as a carbon source, trans-zeatin riboside (TZR) as a cytokinin plant growth regulator, gibberellic acid as a gibberellin plant regulator, and agar as a gelling agent. The pH was adjusted to 5.6 to 5.8 before autoclaving (for further details of the medium composition see Table 2).

Figure 3A:
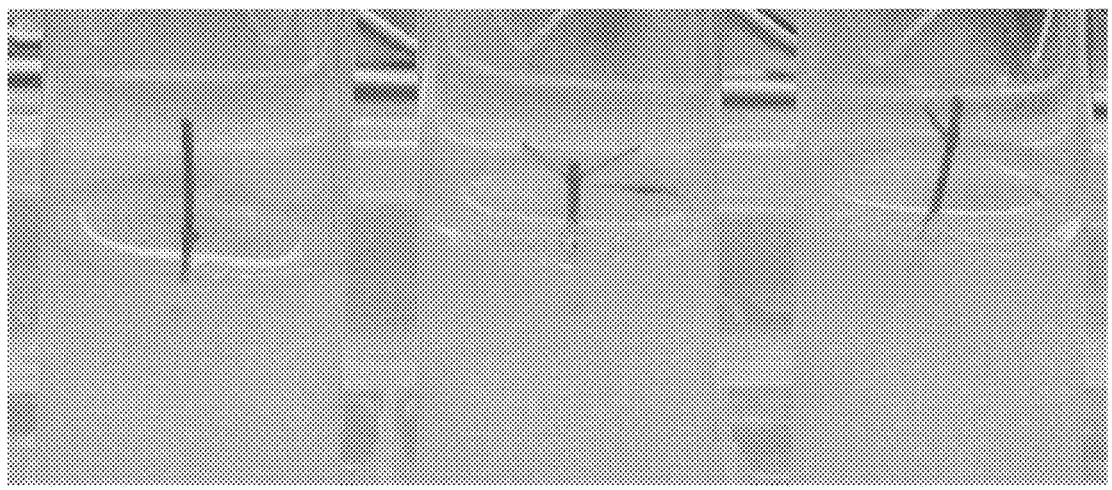
Figure 3B:

Culture tubes containing the nodes were then placed in the growth room at the conditions described in Example 1 for 32 days. Axillary buds were visible above each node at 5 to 10 days, with axillary shoots emerging at 10 to 20 days, and nodes developing on each shoot at 20 to 30 days. (See, FIG. 3). Golden Kush nodes grown on DKWzrg medium at day 0 (FIG. 3A) and after 32 days (FIG. 3B) are shown in triplicate samples. Nodes formed on the axillary shoots lead to enhanced node multiplication and amplifies further micropropagation steps.

Figure 4A:
Figure 4B:

FIG. 4 shows the production of nodes on just DKW (no PGRs) to demonstrate the reduced growth compared to FIG. 3 over the same 32-day growth period. FIG. 5 shows the weighted average efficiency of nodes forming axillary shoots as a percentage on: (A) DKW (black cross-pattern bar) vs. DKWzrg (solid white bar), and (B) MS (black stripped bar) and MSzrg (solid white bar). The efficiency, E[%] is calculated as the number of axillary shoot-forming plantlets, i.e., initiated nodes that form at least one axillary shoot in addition to the stem, per total number of initiated nodes in one experiment. Often following subculture, the main stem will die and two axillary shoots will form. If only one axillary shoot forms and the main stem dies, this is not recorded as an axillary shoot-forming plantlet.

The weighted average of efficiency, wavgE[%] was calculated according to Formula 1:

$$wavgE[\%] = \sum_{i=1}^{n} w_i E[\%]_i \quad \text{Formula 1}$$

Figure 5A:
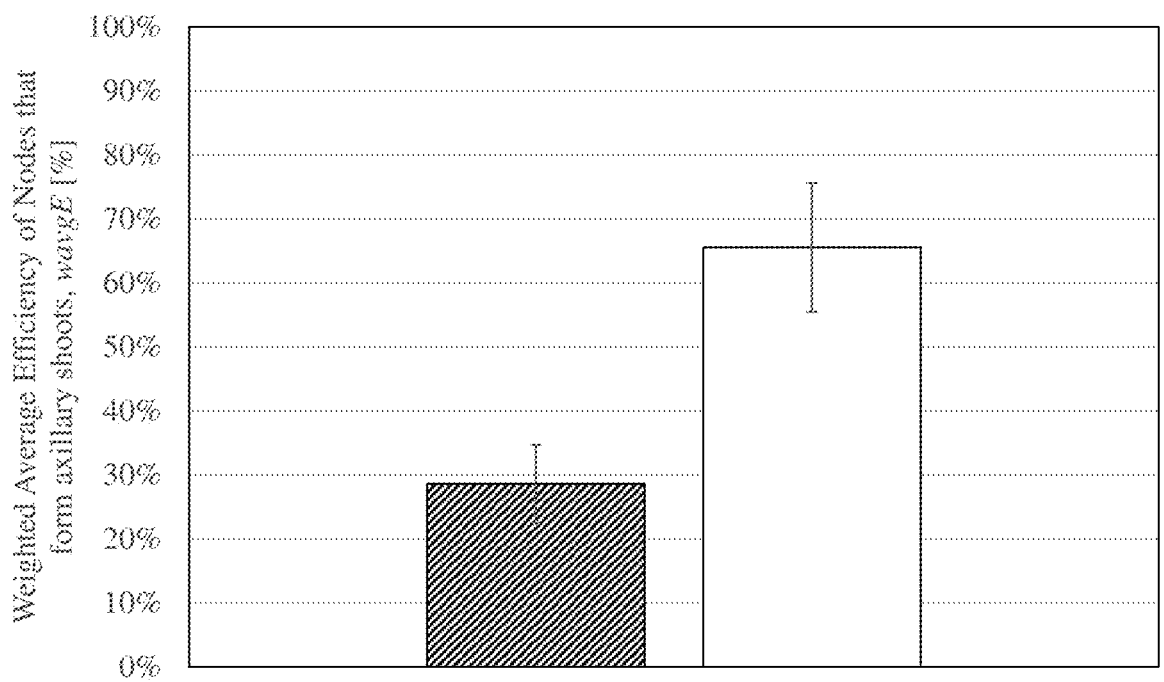
Figure 5B:
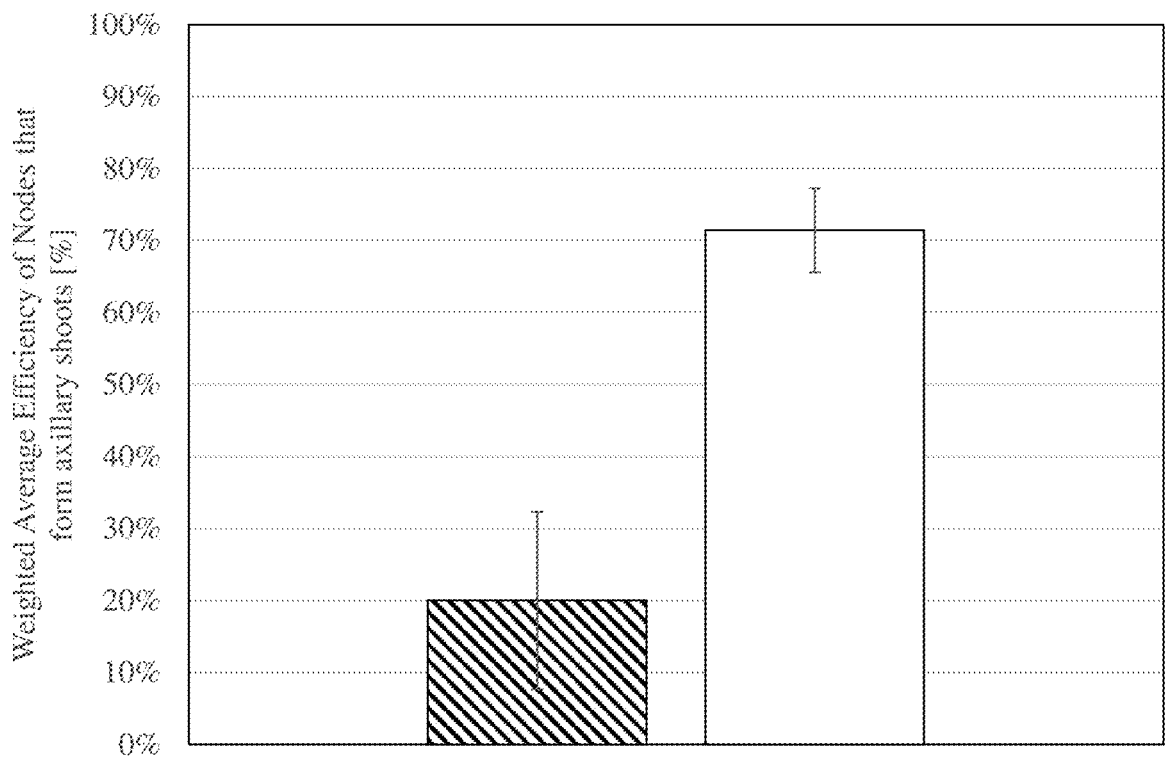

In Formula 1, $w_i$ is calculated as the total number of nodes used in one experiment divided by the total number of nodes, n in all replicates of that treatment. This weighted average is necessary because the total number of nodes used in an experiment rarely are the same. The error bars depicted on FIG. 5A and FIG. 5B are plus or minus one weighted average standard deviation, wavgSD, which was calculated as shown in Formula 2:

$$wavgSD = \sqrt{\frac{\sum_{i=1}^{N} w_i (E[\%]_i - wavgE[\%])^2}{\frac{(N-1)\sum_{i=1}^{N} w_i}{N}}} \quad \text{Formula 2}$$

In Formula 2, N is the total number of different experiments being averaged with non-zero weights. DKWzrg (FIG. 5A) and MSzrg (FIG. 5B), were statistically significantly different on a 95% and 90% confidence interval, respectively from their basal media according to the students t-test. In general, 7 out of 10 plantlets formed axillary shoots on DKWzrg and MSzrg media while the corresponding basal media had only 2 to 3 plantlets out of 10 form axillary shoots.

Table 3, below, shows that an average of 4.3+/−1.4 acceptable nodes for further subculture were formed on DKWzrg, while only 1.7+/−0.6 acceptable nodes on DKW. Values for the acceptable nodes were statistically significantly different on a 99% confidence interval from according to the students t-test. Importantly and surprisingly, for the first time in this experiment, it was shown that the addition of PGR to the DKW medium yielded an average of 2-fold to 3-fold increase in axillary shoots per plantlet in just a single culture interval of about 20 to 30 days. (See, Table 3).

FIG. 6 shows that culture in the presence of the cytokinin, trans-zeatin riboside, and gibberellic acid enhanced the number of acceptable nodes formed as a mixture over the sum of nodes formed by each compound individually. As basal media without plant growth regulators can form axillary shoots and sustain nodal growth even at a lower degree, the net number of nodes formed should be normalized to remove this basal node production, Nbasal. The normalized summation of nodes (net nodes) formed in the presence of each compound individually, Nsum was calculated as shown below in Formula 3.

$$Nsum = (Nc - Nbasal) + (Ng - Nbasal) \quad \text{Formula 3}$$

Figure 6A:
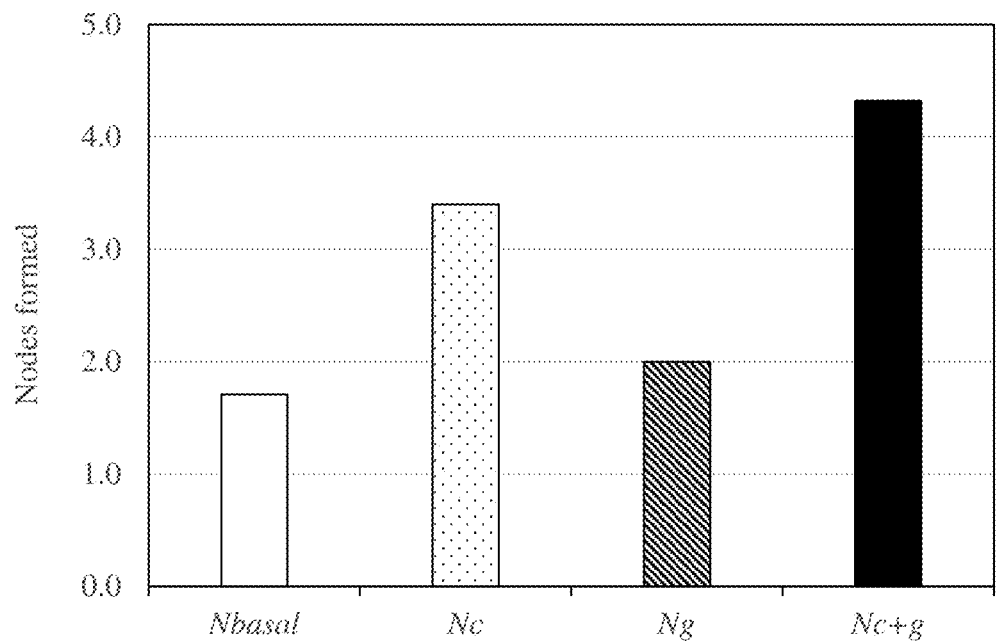
Figure 6B:
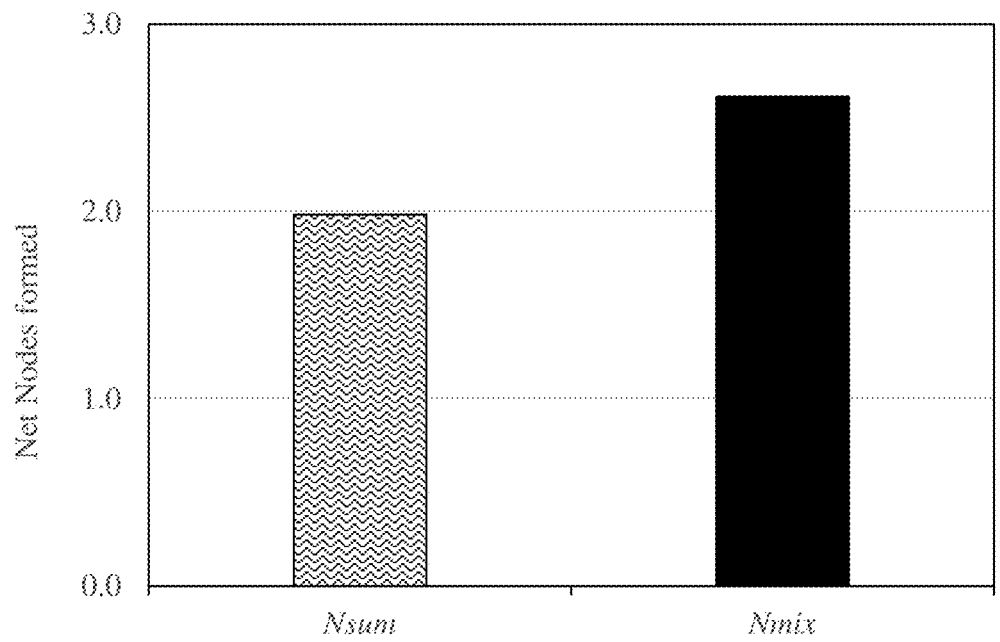

Likewise, the number of nodes formed on basal media was subtracted from the nodes formed in the presence of the two compounds, Nc+g to obtain the net number of nodes formed Nmix. FIG. 6A shows the nodes formed for: Nbasal=DKW with a solid white bar, Nc=DKWzr with a black-dotted pattern bar, Ng=DKWg with a black stripped bar, and Nc+g=DKWzrg with a solid black bar. The DKWg medium was DKWzrg without trans-zeatin riboside, and DKWzr medium was DKWzrg without gibberellic acid. FIG. 6B shows the net nodes formed of Nsum and Nmix. The combination of the gibberellic acid and trans-zeatin riboside as a mixture resulted in more net nodes than the sum of each components net nodes formed which demonstrates a synergetic effect.

Example 4: Continued Axillary Shoot Formation After Four Subcultures

The experiments in this example were aimed at determining whether the nodal explants generated above in Examples 2 and 3 can be repeatably sub-cultured with reproducible results on media with PGRs, and thus establish long-term cultures from the same lineage for amplified *Cannabis* production. This example is therefore aimed at proving an important requirement for commercial micropropagation, specifically, maintaining sustained growth in culture over repeated sub-culturing. This would allow for the consistent multiplication of nodes via shoot production rather than continually initiating ex vitro tissue or germinated seedling shoot tips. If reproducible, this would represent a marked step forward in *Cannabis* culturing and micropropagation as compared with legacy approaches currently in use in the marketplace.

Nodal Golden Kush explants, a minimum of about 1.0 cm in length with leaves cut halfway on the petiole between the leaf blade and stem, were continually sub-cultured onto 20 mL of fresh DKWzrg medium. In another trial performed the same as in Examples 2 and 3, above, a second sub-culture produced new shoots after 25 days on fresh DKWzrg medium. The second subculture on DKWzrg medium was 22 days in duration under the same conditions, and likewise a third, 30 day subculture on DKWzrg medium was completed under the same conditions (data not shown).

Figure 7A:
FIG. 7A and FIG. 7B depict representative Golden Kush nodes showing axillary shoots grown in DKWzrg medium through four subcultures at day 0 (FIG. 7A) and after 31 days of growth (FIG. 7B).
Figure 7B:
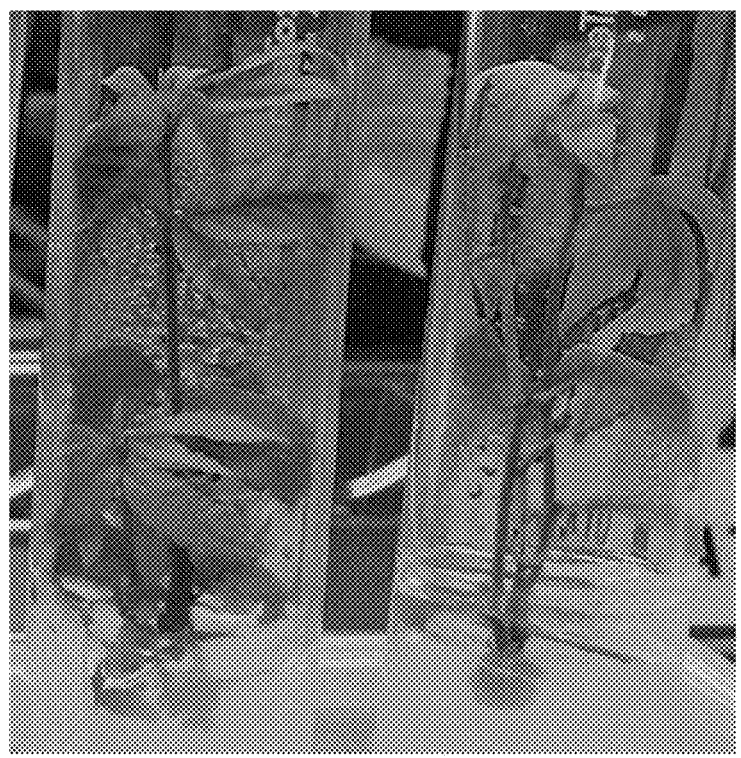

Nodes from the third sub-culture were placed onto fresh DKWzrg medium and grown for 31 days under the same conditions. FIG. 7A shows a photograph of nodes cut from shoots on the third subculture on DKWzrg at day 0, and FIG. 7B shows a photograph of axillary shoots that continued to grow after 31 days. There was some yellowing of tissue observed which suggests the medium may have non-optimal basal nutrient concentrations. However, axillary shoot formation continued despite the basal nutrients being suspected of having non-optimal conditions. Table 3 provides the observed results through four subcultures. The average number of nodes formed are nominally equivalent to the number of nodes induced with DKWzrg the first time. This provides early and strong evidence that the described compositions and methods are suitable to enable commercial micropropagation of plants within Cannabaceae.

TABLE 3

Average No. of Nodes formed (Golden Kush)

| Medium | Average No. Nodes | Standard Deviation |
|---|---|---|
| DKW | 1.7 | 0.6 |
| DKWzrg | 4.3 | 1.4 |
| DKWzr | 3.4 | 1.1 |
| DKWg | 2.0 | 0.6 |
| DKWzrg (thru 4 subcultures) | 4.0 | 1.1 |
| DKWiprg | 4.6 | 2.1 |
| DKWdhzrg (thru 2 subcultures) | 5.0 | 2.1 |
| DKWzrepi | 2.8 | 1.5 |
| DKWtzg | 3.7 | 2.1 |
| DKW2zr2g | 9.0 | 1.7 |
| DKWnh-brg47 | 5.4 | 2.3 |
| DKWnh-mtr28hb | 2.6 | 1.3 |
| QLzrg | 2.3 | 0.5 |
| DKWlzrlg (thru 16-subcultures) | 5.0 | 1.9 |

Example 5: Initiation of Ex Vitro Shoot Tips and Axillary Shoot Formation

This example is aimed at determining whether excised ex vitro shoot tips form axillary shoots after being placed on a basal, e.g., cleansing, medium to reduce apical dominance and to aid in breaking axillary bud dormancy.

Shoot tips from axillary (lateral) stems of Sundae Cake that were 3 to 5 nodes down from the shoot apical meristem on an ex vitro plant in a vegetative state were aseptically cut off in at least 1.0 cm lengths in a laminar flow hood and the leaves were removed by cutting the petiole halfway between the leaf blade and stem.

These Sundae Cake shoot tips were disinfected with 10% (v/v) aqueous solution of CHLOROX® bleach (0.8% sodium hypochlorite solution) also containing 0.25% (v/v) TWEEN® 20 for 10 minutes at room temperature. The disinfectant solution was decanted off and a fresh disinfectant solution was added to the shoot tips again for 10 minutes at room temperature. The shoot tips were then rinsed with a sterile antioxidant solution. The antioxidant solution was autoclaved previous to the rinse and contained 0.15 g/L of citric acid and 0.1 g/L of ascorbic acid in distilled water. The shoot tips were then washed two times with autoclaved distilled water at room temperature.

Each shoot tip was placed on 75 mL of gelled initiation medium in a glass baby food jar with vented caps. The initiation medium was a DKW medium containing full strength DKW macro- and micronutrients plus Gamborg's vitamins, sucrose as a carbon source, and agar as a gelling agent. The pH was adjusted to 5.6 to 5.8 before autoclaving (for further details of the medium composition see Table 2). The shoot tips were then placed in the growth room for 30 days at the conditions described in Example 1.

Nodes on shoots during the growth of the excised shoot tips for 30 days were cut to be at least 1.0 cm in length and the leaves were removed by cutting the petiole halfway between the leaf blade and stem. Each node was placed on 75 mL of a gelled axillary shoot formation medium in a glass baby food jar with vented cap under aseptic conditions (PhytoTech Labs, Lenexa, KS, US). The axillary shoot formation medium in this example was DKWzrg medium.

The DKWzrg medium was full strength DKW macro- and micro-nutrients plus Gamborg's vitamins, sucrose as a carbon source, trans-zeatin riboside as a cytokinin plant growth regulator, gibberellic acid as a gibberellin plant regulator, and agar as a gelling agent. The pH was adjusted to 5.6 to 5.8 before autoclaving (for further details of the medium composition see Table 2). The node cultures were then placed in the growth room at the conditions described in Example 1 for 13 days.

Figure 8:
FIG. 8 is a representative Sundae Cake node grown in DKWzrg medium after 13 days and showing axillary shoot formation.

As shown in FIG. 8, multiple axillary shoots formed in 13 days. This demonstrates that excised ex vitro tissue can form axillary shoots in the same manner as shown in Example 3. This also demonstrates that axillary shoots can be formed in culture for both seedling shoot tips and excised shoot tips from ex vitro vegetative plants.

Example 6: Axillary Shoot Formation on 6-(γ,γ-Dimethylallylamino)purine Riboside This example is aimed at determining whether another cytokinin riboside, such as 6-(γ,γ-dimethylallylamino)purine riboside (iPR), can promote formation of axillary shoots when combined with gibberellic acid at the induction step, as in Example 3. iPR is present naturally in a wide array of plant species, and this example explores whether other naturally-present cytokinin ribosides can achieve the same effect as trans-zeatin riboside (tZR).

As described in Example 2, Golden Kush shoots containing nodes developed during the growth of the seedling shoot tips for 30 days were aseptically cut to be at least 1.0 cm in length and the leaves were removed by cutting the petiole halfway between the leaf blade and stem. Each node was placed on 20 mL of gelled axillary shoot formation medium in a culture tube. This medium was DKWiprg (see Table 2).

The DKWiprg medium was full strength DKW macro- and micro-nutrients plus Gamborg's vitamins, sucrose as a carbon source, 6-(γ,γ-dimethylallylamino)purine riboside (iPR) as a cytokinin plant growth regulator, gibberellic acid as a gibberellin plant regulator, and agar as a gelling agent. The pH was adjusted to 5.6 to 5.8 before autoclaving (for further details of the medium composition see Table 2).

Figure 9A:
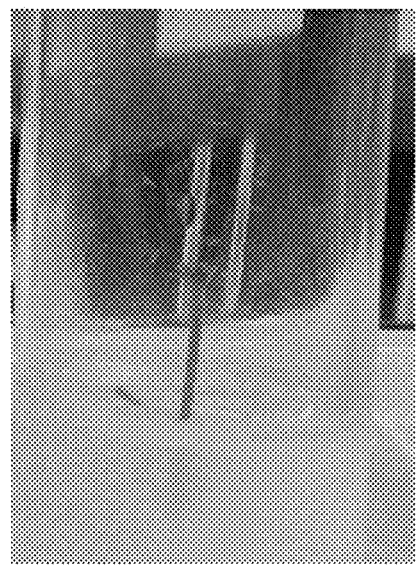
FIG. 9A and FIG. 9B show a representative Golden Kush node grown in DKWiprg medium at day 0 (FIG. 9A) and after 32 days of growth (FIG. 9B), yielding an axillary shoot in DKWiprg medium following subculture after a single node was cut from a grown seeding shoot tip initiated on cleansing medium (DKW with no PGR).
Figure 9B:
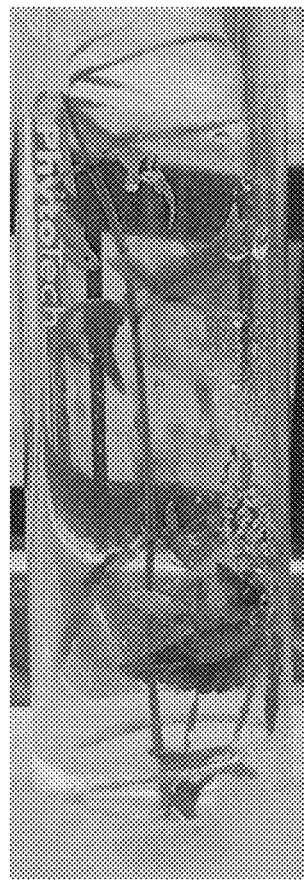

The Golden Kush nodes were then placed in the growth room at the conditions described in Example 1 for 32 days. FIG. 9A shows representative Golden Kush starting nodes at day 0, while FIG. 9B shows the progression of growth of the same plantlets after 32 days. Axillary shoots formed on DKWiprg medium as was observed in Example 3. Approximately 4.6+/−2.1 acceptable nodes formed per plantlet initiated across this experiment. (See, Table 3). These data demonstrate that cytokinin ribosides other than tZR, paired with a gibberellin, also enhance axillary shoot formation.

Example 7: Axillary Shoot Formation on dHZR

This example is aimed at determining whether dihydrozeatin riboside (dHZR) can stimulate formation of axillary shoots in plantlets when it is combined with gibberellic acid. dHZR is present naturally in a wide-array of plants and this example, like Example 6, also explores whether other naturally-present cytokinin ribosides can achieve the same effect as observed with tZR. In this example, repeated axillary shoot formation after PGR induction was also investigated.

As described in Example 2, Golden Kush shoots consisting of multiple nodes developed during the growth of the seedling shoot tips for 30 days, were cut to be at least 1.0 cm in length and the leaves were removed by cutting the petiole halfway between the leaf blade and stem. Each node was placed on 20 mL of a gelled axillary shoot formation medium in a culture tube. This medium was DKWdhzrg.

The DKWdhzrg medium was full strength DKW macro- and micro-nutrients plus Gamborg's vitamins, sucrose as a carbon source, dihydrozeatin riboside (dHZR) as a cytokinin plant growth regulator, gibberellic acid as a gibberellin plant regulator, and agar as a gelling agent. The pH was adjusted to 5.6 to 5.8 before autoclaving (for further details of the medium composition see Table 2).

Figure 10A:
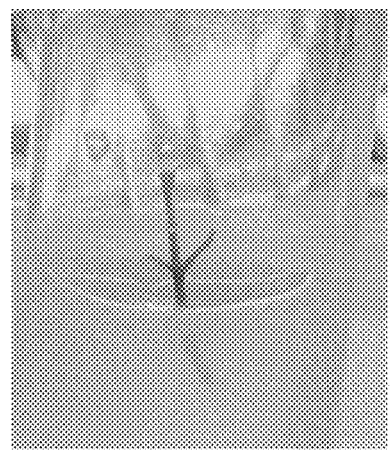
FIG. 10A and FIG. 10B show a representative Golden Kush node grown in DKWdhzrg medium that has formed axillary shoots through two subcultures at day 0 (FIG. 10A) and after 30 days of growth (FIG. 10B). This plantlet produced an axillary shoot in DKWdhzrg medium following subculture after a single node was cut from a seeding shoot tip grown on cleansing DKW medium (FIG. 2B).
Figure 10B:

As described in Examples 2 and 3, above, a second sub-culture onto 20 mL of fresh, gelled DKWdhzrg medium was carried out after 24 days on the first PGR induction. The node cultures were then placed in the growth room at the conditions described in Example 1 for 30 days. FIG. 10A shows representative starting nodes on plantlets at day 0, and in FIG. 10B the progression of growth after 30 days. Axillary shoots formed on DKWdhzrg medium as was seen in Example 3. Approximately 5.0+/−2.1 acceptable nodes formed per plantlet initiated across this experiment provides further evidence that cytokinin ribosides paired with a gibberellin in the medium enhances multiplication of axillary shoots. (See, Table 3).

Example 8: Axillary Shoot Formation with Brassinolides

Brassinolides and gibberellins have been reported to share similar biological functions in vivo. (See, Unterholzner et al., *Plant Cell*, 27(8):2261-72, 2015). In recent years it has been shown that brassinolides are involved in gibberellin biosynthesis and metabolism. This example is therefore aimed at determining whether a representative brassinolide, such as 2,4 epibrassinolide, stimulates formation of axillary shoot growth on plants when combined with trans-zeatin riboside (tZR) at the PGR induction step.

As described in Example 2, Golden Kush developed shoots with multiple nodes during the growth of the seedling shoot tips for 30 days. These nodes were cut to be at least 1.0 cm in length and the leaves were removed by cutting the petiole halfway between the leaf blade and stem. Each node was placed on 20 mL of a gelled axillary shoot formation medium in a culture tube. This was in DKWzrepi medium.

The DKWzrepi medium was full strength DKW macro- and micro-nutrients plus Gamborg's vitamins, sucrose as a carbon source, trans-zeatin riboside (tZR) as a cytokinin plant growth regulator, 2,4-epibrassinolide as a brassinolide plant regulator, and agar as a gelling agent. The pH was adjusted to 5.6 to 5.8 before autoclaving (for further details of the medium composition see Table 2).

Figure 11A:
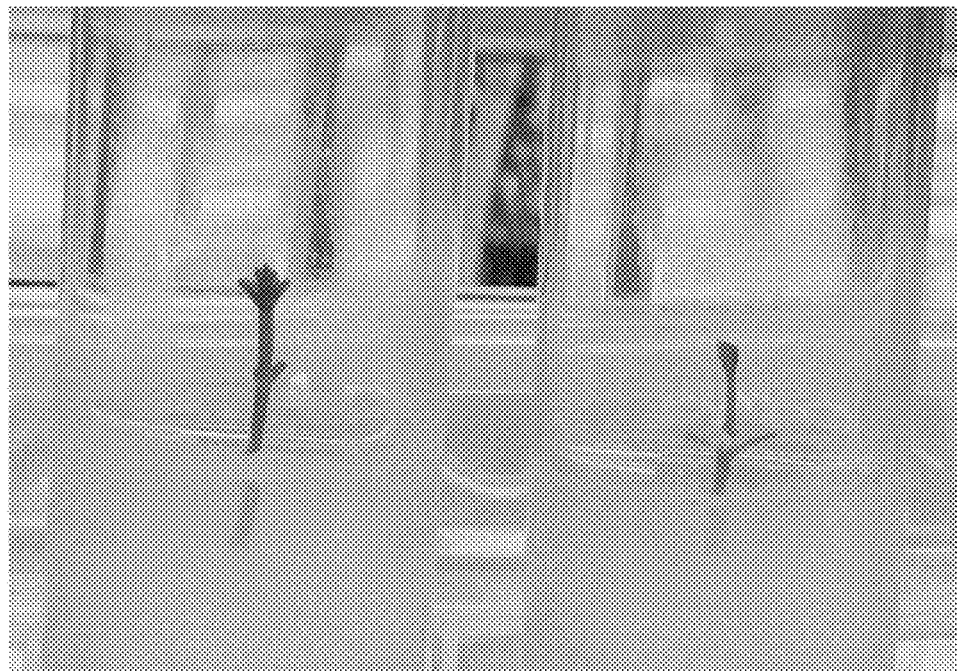
FIG. 11A and FIG. 11B show representative Golden Kush nodes at day 0 (FIG. 11A) and after 32 days (FIG. 11B) yielding axillary shoots in DKWzrepi medium following subculture from single nodes cut from elongated seeding shoot tips initiated on DKW medium.
Figure 11B:
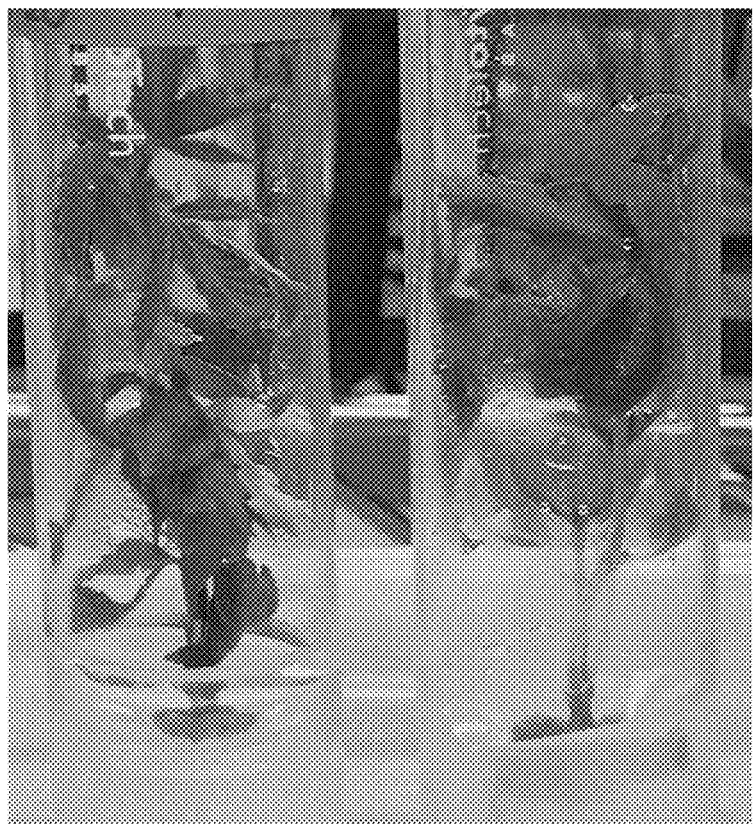

The nodes were then placed in the growth room at the conditions described in Example 1 for 32 days. FIG. 11A shows representative Golden Kush nodes at day 0, and FIG. 11B shows axillary shoot growth after 24 days in the DKWzrepi medium. Axillary shoots formed on this medium as also seen in Example 3. The number of nodes produced are shown in Table 3. This experiment demonstrates that brassinolides can act as a replacement for gibberellins in the PGR mixture and still stimulate production of axillary shoot production.

Example 9: Axillary Shoot Formation with a Cytokinin Base

Cytokinin bases, such trans-zeatin are the chemically active structural form of the cytokinin that binds to subcellular receptors and induces signal transduction to produce biological effects that are attributed to cytokinins, e.g., increase cell division, delay senescence, and promote axillary shoots. This example is therefore aimed at determining whether trans-zeatin as a cytokinin base at an equimolar concentration to trans-zeatin riboside in Example 3 can similarly trigger formation of axillary shoots when combined with gibberellic acid at the PGR induction step.

As described in Example 2, Golden Kush shoots including nodes developed during the growth of the seedling shoot tips for 30 days were cut to be at least 1.0 cm in length and the leaves were removed by cutting the petiole halfway between the leaf blade and stem. Each node was placed on 20 mL of a gelled axillary shoot formation medium in a culture tube. This was in DKWtzg medium.

The DKWtzg medium was full strength DKW macro- and micro-nutrients plus Gamborg's vitamins, sucrose as a carbon source, trans-zeatin (tZ) as a cytokinin plant growth regulator, gibberellic acid as a gibberellin plant regulator, and agar as a gelling agent. The pH was adjusted to 5.6 to 5.8 before autoclaving (for further details of the medium composition see Table 2).

Figure 12A:
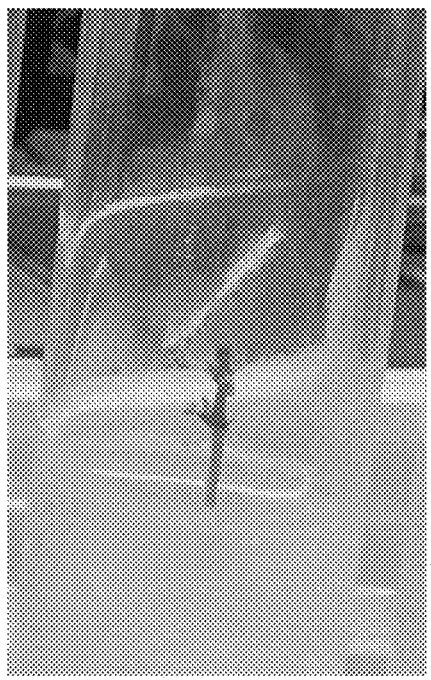
FIG. 12A and FIG. 12B depict a representative Golden Kush node at day 0 (FIG. 12A) and after 32 days of growth (FIG. 12B) producing an axillary shoot from a node in DKWtzg medium following subculture from a single node cut from an elongated seeding shoot tip initiated on DKW medium.
Figure 12B:

The Golden Kush nodes in culture tubes were then placed in the growth room at the conditions described in Example 1 for 32 days. FIG. 12A shows a photograph of a representative Golden Kush starting node at day 0, and FIG. 12B shows a photograph of representative plant material after 32 days. Once again, axillary shoots formed on DKWtz medium as observed in Example 3, and the quantity of nodes produced is reflected in Table 3. This experiment therefore conclusively demonstrates that the cytokinin bases paired with gibberellin in the PGR mixture produce axillary shoots for further micropropagation.

Example 10: Axillary Shoot Formation at Higher tZR and GA$_3$ Concentrations

This example is aimed at determining whether trans-zeatin riboside and GA$_3$ at higher concentrations can enhance the number of axillary shoots compared to Example 3.

As described in Example 2, Golden Kush shoots developed comprising nodes during the growth of the seedling shoot tips for 30 days were cut to be at least 1.0 cm in length and the leaves were removed by cutting the petiole halfway between the leaf blade and stem. Each node was placed on 20 mL of a gelled axillary shoot formation medium in a culture tube. The medium was DKW2zr2g.

The DKW2zr2g medium was full strength DKW macro- and micro-nutrients plus Gamborg's vitamins, sucrose as a carbon source, trans-zeatin riboside (tZR) as a cytokinin plant growth regulator, gibberellic acid as a gibberellin plant regulator, and agar as a gelling agent. The pH was adjusted to 5.6 to 5.8 before autoclaving (for further details of the medium composition see Table 2).

Figure 13A:
FIG. 13A and FIG. 13B show Golden Kush nodes yielding multiple axillary shoots from a single node in DKW2zr2g medium following subculture of seeding shoot tips initiated on DKW medium at day 0 (FIG. 13A) and after 27 days of growth (FIG. 13B). Approximately 5 axillary shoots per node was produced on this medium.
Figure 13B:

The Golden Kush nodes in culture tubes were then placed in the growth room at the conditions described in Example 1 for 31 days. FIG. 13A shows a photograph of a representative starting node at day 0, and FIG. 13B shows a photograph of the progression of growth from the same node after 27 days. Axillary shoots formed on DKW2zr2g medium most surprisingly created twice as many nodes (9.0+/−1.7 nodes formed) as observed in Example 3. (See also, Table 3).

This experiment demonstrates that increasing the cytokinin riboside and gibberellin concentration in the PGR mixture markedly enhances axillary shoot formation, and ultimately increases the number of nodes produced that was available for further micropropagation.

Example 11: Exposure to Cleansing Media Prior to PGR Induction

This example is aimed at determining the impact of cleansing medium without PGRs prior to induction of formation and growth of axillary shoots in *Cannabis* with cytokinins and gibberellic acid and/or brassinolide. In this example, Golden Kush-germinated seedling shoot tips were inoculated directly onto a medium containing trans-zeatin riboside and gibberellic acid with no initial cleansing step, as in Example 2. Thus, essentially this experiment is aimed at determining if axillary shoot formation can occur when the procedure outlined in Example 2 is skipped.

As described in Example 2, seedling shoot tips were cut to a size of 1.0 cm in length per piece of tissue. These trimmings included the cotyledons and the shoot apical meristem. Each shoot tip was placed on 20 mL of a gelled axillary shoot formation medium in a culture tube. This medium was DKWzrg.

The DKWzrg medium was full strength DKW macro- and micro-nutrients plus Gamborg's vitamins, sucrose as a carbon source, trans-zeatin riboside as a cytokinin plant growth regulator, gibberellic acid as a gibberellin plant regulator, and agar as a gelling agent. The pH was adjusted to 5.6 to 5.8 before autoclaving (for further details of the medium composition see Table 2).

The Golden Kush nodes in culture tubes were then placed in the growth room at the conditions described in Example 1 for 31 days. Representative starting nodes at day 0 are shown in FIG. 14A, and FIG. 14B shows a photograph of the progression of growth of the same axillary shoots after 31 days.

Figure 14A:
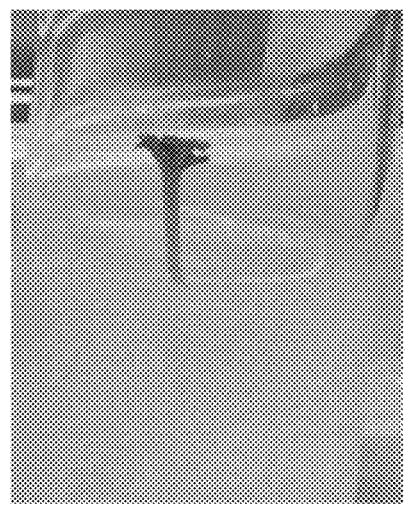
FIG. 14A and FIG. 14B show a representative Golden Kush node that produced no axillary shoots when initiated directly onto DKWzrg medium without initial culture on cleansing medium at day 0 (FIG. 14A) and after 31 days of growth (FIG. 14B). This illustrates the necessity for the cleansing step in forming axillary shoots.
Figure 14B:
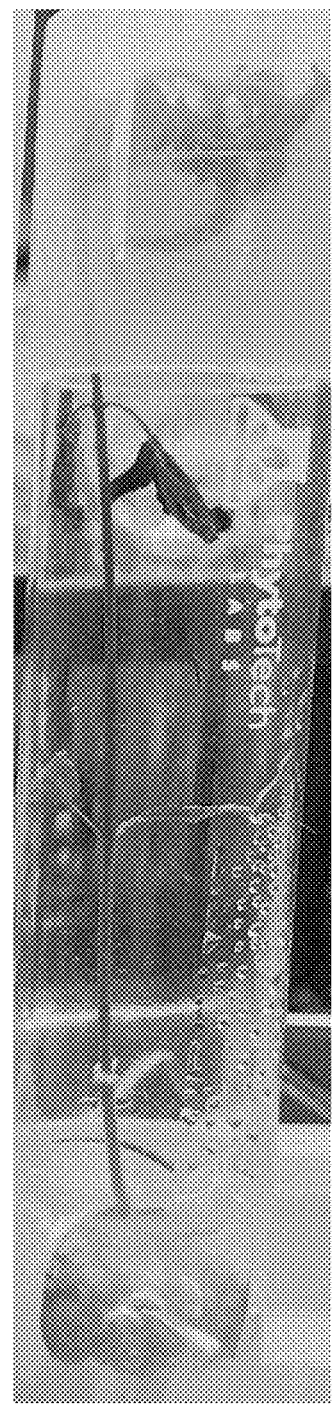

As is readily apparent from FIGS. 14A and 14B, axillary shoots were not formed in a robust manner on DKWzrg medium when the cleansing step was skipped. These data demonstrate that growth on a cleansing medium for some time period prior to inducing shoots with the combination of PGRs, trans-zeatin riboside, and gibberellic acid, is beneficial to aiding formation of axillary shoots from a single node.

Example 12: Impact of Apical Dominance on Successive Subcultures on Cleansing Media This example investigated whether a cleansing medium, DKW, containing no added PGRs, could reduce apical dominance in Golden Kush tissue during successive subcultures from a seedling to sectioned nodes.

Golden Kush seedlings were grown to approximately 10 cm to 13 cm in height for 19 days, as detailed in Example 1, and the shoot tips were then cut to a size of about 1.0 cm in length per piece of tissue that included the cotyledons and shoot apical meristem. Each shoot tip was transferred to 20 mL of gelled DKW basal medium contained in a sterile culture tube in a laminar flow hood. Each shoot tip was placed vertically into the medium with the cotyledon and shoot apical meristem approximately 0.2 cm above the medium surface. The Golden Kush seedling shoot tips in culture tubes were then placed in the growth room at the conditions described in Example 1 for 31 days.

DKW basal medium included full-strength DKW macro- and micronutrients plus Gamborg's vitamins, sucrose as a carbon source, and agar as a gelling agent. The pH was adjusted to approximately 5.6 to 5.8 before autoclaving (for further details of the medium composition, see Table 2).

Shoots comprising multiple nodes developed during the growth of the seedling shoot tips for 31 days. The nodes were cut to be at least 1.0 cm in length and the leaves were removed by cutting the petiole halfway between the leaf blade and stem. Each node was placed on fresh 20 mL of DKW gelled basal medium in a culture tube. The nodes were then placed in the growth room at the conditions described in Example 1 for 32 days.

FIG. 15 shows the successive reduction in plant height of a representative seedling phenotype, A9, transferred to cleansing medium two times. FIG. 15A shows a representative seedling phenotype denoted A9 after 19 days of germination. The strong apical dominance is noted in this seedling as evidenced by the fact that there are no leaf junctions formed and that the shoot tip reached the top of the test tube. FIG. 15B shows the reduction in total plantlet height after the seedling shoot tip was cultured for 31 days on DKW. A further reduction in total plant height after 32 days is depicted in FIG. 15C, which shows a photograph of a representative node sectioned from the grown seedling shoot tip from FIG. 15B. Example 11 shows that in the absence of the cleansing medium treatment, the seedling failed to generate axillary shoots when initiating seedling shoot tips directly on DKWzrg. This example provides evidence that the cleansing media step reduces apical dominance and possibly encourages breaking axillary bud dormancy.

Example 13: Axillary Shoot Formation on Benzyladenine Riboside and Gibberellin This example is aimed at determining whether another representative cytokinin riboside, such as benzyladenine riboside (BAR), can promote formation of axillary shoots when combined with gibberellins $GA_4+GA_7$ at the induction step, as in Example 3. This example explores whether synthetic cytokinin ribosides can achieve the same effect as the natural cytokinin trans-zeatin riboside (tZR).

As described in Example 2, Golden Kush nodes developed during the growth of the seedling shoot tips for 30 days were aseptically cut to be at least 1.0 cm in length and the leaves were removed by cutting the petiole halfway between the leaf blade and stem. Each Golden Kush node was placed on 20 mL of a gelled axillary shoot formation medium in a culture tube. This medium was DKWnh-brg47. (See, Table 2).

The DKWnh-brg47 medium contained modified-DKW macro- and micro-nutrients plus Gamborg's vitamins, sucrose, benzyladenine riboside (BAR) as a cytokinin plant growth regulator, gibberellins $GA_4+GA_7$ as a gibberellin plant regulator, and agar as a gelling agent. The pH was adjusted to 5.6 to 5.8 before autoclaving (for further details of the medium composition see Table 2).

The nodes in culture tubes were then placed in the growth room at the conditions described in Example 1 for 28 days. FIG. 16A shows a photograph of representative starting nodes at day 0, and FIG. 16B shows a photograph of the progression of growth of the same plantlets after 28 days. Axillary shoots formed on DKWnh-brg47 medium as was observed in Example 3. Approximately 5.4+/−2.3 acceptable nodes formed per plantlet initiated across this experiment. (See, Table 3). These data demonstrate that a synthetic cytokinin riboside, paired with a gibberellin, also enhances multiplication of nodes with axillary shoots for further micropropagation.

Example 14: Axillary Shoot Formation in 28-Homobrassinolide and Cytokinin Riboside This example is aimed at determining whether another representative cytokinin riboside, such as meta-topolin riboside (mTR), can promote formation of axillary shoots when combined with an alternate brassinolide, 28-homobrassinolide, as in Example 8.

As described in Example 2, Golden Kush nodes developed during the growth of the seedling shoot tips for 30 days were aseptically cut to be at least 1.0 cm in length and the leaves were removed by cutting the petiole halfway between the leaf blade and stem. Each node was placed on 20 mL of a gelled axillary shoot formation medium in a culture tube. This medium was DKWnh-mtr28hb. (See, Table 2).

The DKWnh-mtr28hb medium contained modified-DKW macro- and micro-nutrients plus Gamborg's vitamins, sucrose as a carbon source, meta-topolin riboside (mTR) as a cytokinin plant growth regulator, 28-homobrassinolide as a brassinolide plant regulator, and agar as a gelling agent. The pH was adjusted to 5.6 to 5.8 before autoclaving (for further details of the medium composition see Table 2).

The nodes in culture tubes were then placed in the growth room at the conditions described in Example 1 for 28 days. FIG. 17A shows a photograph of representative starting nodes at day 0, and FIG. 17B shows a photograph of the progression of growth of an axillary shoot after 28 days. Axillary shoots formed on DKWnh-mtr28hb medium, as was also observed in Example 3. Approximately 2.6+/−1.3 acceptable nodes formed per plantlet initiated across this experiment. (See, Table 3). This experiment demonstrates that alternative brassinolides act as functional replacements for gibberellins in the PGR mixture and stimulate production of axillary shoots for further micropropagation.

Example 15: Initiation of Ex Vitro Shoot Tips and Axillary Shoot Formation

This example is aimed at determining whether another *Cannabis* variety of excised ex vitro shoot tips (Mandarin Cookies) can form axillary shoots after being placed on a basal medium to reduce apical dominance and to aid in promoting axillary bud formation.

As described in Example 2 and Example 5, Mandarin Cookies nodes developed during the growth of the ex vitro shoot tips for 30 days were aseptically cut at least 1.0 cm in length and the leaves were removed by cutting the petiole halfway between the leaf blade and stem. Each node was placed on 75 mL of a gelled initiation medium in a glass baby food jar with vented caps. This medium was DKWnhzrg (see Table 2).

The DKWnhzrg medium was modified-DKW macro- and micro-nutrients plus Gamborg's vitamins, sucrose as a carbon source, trans-zeatin riboside as a cytokinin plant growth regulator, gibberellic acid as a gibberellin plant regulator, and agar as a gelling agent. The pH was adjusted to 5.6 to 5.8 before autoclaving (for further details of the medium composition see Table 2). The nodes were then placed in the growth room at the conditions described in Example 1 for 19 days.

As shown in FIG. 18, multiple axillary shoots formed in 19 days. This confirms that other varieties of excised ex vitro tissue form axillary shoots in the same manner as shown in Example 5. These data also provide further evidence that axillary shoots are formed in culture from ex vitro vegetative shoot tips as those from seedling shoot tips.

Example 16: Axillary Shoot Induction on Quoirin and Lepoivre

This example demonstrates a broader range of medium nutrient concentrations over which cytokinin ribosides and gibberellins/brassinolides induce axillary shoots in Cannabaceae. Quoirin and Lepoivre is a basal salt mixture comprising relatively higher calcium levels. (See, Quoirin, M. and Lepoivre, P., *Acta Hortic.*, 78:437-442, 1977).

As described in Example 2, Golden Kush nodes, developed during the growth of the seedling shoot tips for 30 days, were aseptically cut to be at least 1.0 cm in length and the leaves were removed by cutting the petiole halfway between the leaf blade and stem. Each node was placed on 20 mL of a gelled axillary shoot formation medium in a culture tube. This medium was QLzrg. (See, Table 2).

The QLzrg medium contained Quoirin and Lepoivre macro- and micro-nutrients plus Gamborg's vitamins, sucrose as a carbon source, trans-Zeatin riboside (tZR) as a cytokinin plant growth regulator, gibberellic acid as a gibberellin plant regulator, and agar as a gelling agent. The pH was adjusted to 5.6 to 5.8 before autoclaving (for further details of the medium composition see Table 2).

The nodes in culture tubes were then placed in the growth room at the conditions described in Example 1 for 29 days. FIG. 19A shows a photograph of representative starting nodes at day 0, and FIG. 19B shows a photograph of the progression of growth of the same plantlet after 29 days. Axillary shoots formed on QLzrg medium as was observed in Example 3. Approximately 2.3+/−0.5 acceptable nodes formed per plantlet initiated in this experiment. (See, Table 3). This experiment demonstrates that alternative plant tissue culture media formulations function equally as well with cytokinin ribosides and gibberellins or brassinolides in stimulating production of axillary shoots.

Example 17: Initiation of Ex Vitro Shoot Tips and Axillary Shoot Formation

This example is aimed at determining whether another *Cannabis* variety, White Shark, introduced to culture from ex vitro shoot tips can form axillary shoots over repeated subcultures.

White Shark nodes developed during the growth of the ex vitro shoot tips for 28 days were aseptically cut to be at least 1.0 cm in length and the leaves were removed by cutting the petiole halfway between the leaf blade and stem, as described in Example 2 and Example 5. Each node was placed on 75 mL of a gelled initiation medium in a glass baby food jar with vented caps. This medium was DKW1zr1g.

The DKW1zr1g medium was full strength DKW macro- and micro-nutrients plus Gamborg's vitamins, sucrose, trans-zeatin riboside as a cytokinin plant growth regulator, gibberellic acid as a gibberellin plant regulator, and agar as a gelling agent. The pH was adjusted to 5.6 to 5.8 before autoclaving (for further details of the medium composition see Table 2).

White Shark shoots containing multiple nodes from shoots grown on DKW1zr1g were repeatedly sub-cultured over 5 months, as described in Example 4. The time on media between subcultures was 27 days to 29 days. Nodes from White Shark No. 3 shoots grown on DKW could only be sub-cultured 3 times due to lack of elongation. Internodal spacing decreased successively after each subculture on DKW.

Nodes cut from tissue that had been sub-cultured on DKW1zr1g medium were then placed in the growth room at the conditions described in Example 1 for 28 days. FIG. 20A shows a photograph of representative starting nodes at day 0, and FIG. 20B shows a photograph of the progression of growth of the same plantlets after 28 days.

FIG. 20B also shows the nodes initially formed from axillary shoots after 6 subcultures on medium containing trans-zeatin riboside and gibberellic acid. The average plantlet generated 3.3 nodes after 28 days. These data demonstrate that combination of cytokinin ribosides and gibberellins supports the repeated subcultures of multiple varieties of Cannabaceae, both from seedling shoot-tip and ex vitro donor plants.

Example 18: Long-Term Maintenance in Multiplication Phase

This example shows that the combination of cytokinin ribosides and gibberellins can support nodes being maintained for more than 1 year and 5 months on PGR-containing media. This example also shows that cytokinin riboside and gibberellin concentrations can be increased and enhance node production.

As described in Example 4 and Example 17, Golden Kush nodes from shoots grown on DKWzrg were repeatedly sub-cultured over the course of 1 year (1 subculture on cleansing medium with 11 subcultures on DKWzrg medium). The time on media between subcultures was 22 days to 34 days over the course of 11 months.

Nodes from shoots produced during the 11$^{th}$ subculture on DKWzrg were cut and half were continued on DKWzrg medium, and half were placed on DKW1zr1g medium. Shoots were grown and nodes sub-cultured on each medium for 5 more subcultures. Nodes on each medium were sub-cultured on the same days, and the time on media ranged from was 27 to 33 days over the course of 5 months.

Nodes from Golden Kush plantlets grown on DKW could only be sub-cultured 5 times due to lack of elongation. Internodal spacing decreased successively after each sub-culture on DKW. Nodes cut from shoots that had been sub-cultured on DKWzrg medium were then placed on DKW1zr1g (See Table 2) medium in the growth room at the conditions described in Example 1 for 27 days. FIG. 21A shows representative starting node at day 0, while FIG. 21B depicts the progression of shoot growth of the same plantlet after 19 days.

Shoots generated an average of 5.0+/−1.9 nodes after 27 days on DKW1zr1g after 16 subcultures on PGRs. Table 4, below, shows that there was slight enhancement of nodal production on DKW1zr1g over DKWzrg during 5 subcultures. These data demonstrate that the combination of cytokinin ribosides and gibberellins supports repeated subcultures for about 17 months, and that boosting the concentration provides improvement in node production.

TABLE 4

Golden Kush Node Production

| Medium Subculture No. on PGRs | DKWzrg | | DKW1zr1g | |
|---|---|---|---|---|
| | Average No. Nodes | Standard Deviation of No. Nodes | Average No. Nodes | Standard Deviation of No. Nodes |
| 12 | 3.9 | 0.8 | 4.6 | 0.9 |
| 13 | 3.3 | 0.7 | 4.4 | 0.5 |
| 14 | 3.9 | 0.6 | 4.8 | 0.8 |
| 15 | 3.8 | 0.8 | 5.4 | 1.7 |
| 16 | 4.1 | 0.7 | 5.0 | 1.9 |

The breadth and scope of the present disclosure should not be limited by any of the above-described exemplary embodiments, but should be defined only in accordance with the following claims and their equivalents. That is, the above examples are included to demonstrate various exemplary embodiments of the described methods and systems. It will be appreciated by those of skill in the art that the techniques disclosed in the examples represent techniques discovered by the inventor to function well in the practice of the described methods and compositions, and thus can be considered to constitute optional or exemplary modes for its practice. However, those of skill in the art will, in light of the present disclosure, appreciate that many changes can be made in these specific embodiments that are disclosed and still obtain a like or similar result without departing from the spirit and scope of the described methods and compositions.

What is claimed is:

1. A composition comprising a plant tissue from a Cannabaceae plant and a sterile culture medium comprising:
    (i) a basal plant medium, wherein the basal plant medium is Driver Kuniyaki Walnut (DKW) medium,
    (ii) one or more ribosides selected from 6-(3,3-dimethylallylamino)-9-0-D-ribofuranosylpurine (iPR), 6-((E)-4-hydroxy-3-methylbut-2-enylamino)-9-0-D-ribofuranosylpurine (tZR), and 6-(4-hydroxy-3-methylbutylamino)-9-O-D-ribofuranosylpurine (DHZR), and
    (iii) gibberellic acid A3,
    wherein the culture medium is essentially free of auxins,
    wherein the culture medium stimulates axillary shoot growth of Cannabaceae grown in a sterile tissue culture to a greater extent than Cannabaceae grown in the sterile tissue culture without the culture medium, and
    wherein the culture medium stimulates axillary shoot growth of Cannabaceae grown in the sterile tissue culture to a greater extent than DKW medium.

2. The composition of claim 1, wherein the composition further comprises one or more brassinolides.

3. The composition of claim 1, wherein the culture medium stimulates axillary shoot growth of Cannabaceae grown in sterile tissue culture at a rate of approximately 1.5 nodes or more per month more than Cannabaceae grown in sterile tissue culture without the culture medium.

4. The composition of claim 1, wherein the one or more ribosides are present in a concentration of from 0.1 μM to 6.0 μM.

5. The composition of claim 1, wherein the one or more ribosides is iPR or tZR.

6. The composition of claim 1, wherein the culture medium stimulates axillary shoot growth of Cannabaceae grown in sterile tissue culture at a rate of approximately 2.8 nodes or more per month more than Cannabaceae grown in sterile tissue culture without the culture medium.

7. The composition of claim 1, wherein the one or more ribosides are present in a concentration of from 0.1 µM to 30 µM.

8. The composition of claim 1, wherein the gibberellic acid A3 is present in a concentration of from 0.1 µM to 9.0 µM.

9. The composition of claim 2, wherein the one or more brassinolides are one or more of 2,4-epi-brassinolide, 2,8-homo-brassionolide, and 2,4-epi-castasterone.

10. The composition of claim 1, wherein the culture medium further comprises one or more of: vitamins, carbohydrates, buffers, amino acids, complex organic ingredients, salts, and gelling agents.

11. The composition of claim 1, wherein the culture medium further comprises a gelling agent that is one or more of agar, gellan gum, xantham gum, guar gum, gum arabic, agargellan, and carrageenan.

12. A plant tissue culture comprising a plant tissue excised from a Cannabaceae plant and a culture medium;
wherein the culture medium is a sterile composition comprising:
(i) a basal plant medium, wherein the basal plant medium is Driver Kuniyaki Walnut (DKW) medium,
(ii) one or more ribosides, wherein the one or more ribosides is selected from 6-(3,3-dimethylallylamino)-9-β-D-ribofuranosylpurine (iPR), 6-((E)-4-hydroxy-3-methylbut-2-enylamino)-9-β-D-ribofuranosylpurine (tZR), and 6-(4-hydroxy-3-methylbutylamino)-9-β-D-ribofuranosylpurine (DHZR), and
(iii) gibberellic acid $A_3$,
wherein the gibberellic acid $A_3$ is present in the composition in a concentration of from 0.5 µM to about 7.0 µM or from about 1.0 µM to about 7.5 µM
wherein the composition stimulates axillary shoot growth of Cannabaceae grown in the tissue culture to a greater extent than Cannabaceae grown in sterile tissue culture without the composition.

13. The plant tissue culture of claim 12,
wherein the basal plant medium further comprises one or more of the following components:
$Mg^{2+}$ at a concentration of from about 0.10 mM to about 10 mM;
$SO_4^{2-}$ at a concentration of from about 0.1 mM to about 15 mM;
$Ca^{2+}$ at a concentration of from about 0.1 mM to about 10 mM;
$K^+$ at a concentration of from about 1 mM to about 40 mM;
$PO_4^{3-}$ at a concentration of from about 0.1 mM to about 10 mM;
iron at a concentration of from about $1 \times 10^{-3}$ mM to about 1.0 mM; and
EDTA at a concentration of from about $1 \times 10^{-3}$ mM to about 1 mM.

14. The plant tissue culture of claim 12, further comprising:
(iv) one or more brassinolides.

15. The plant tissue culture of claim 12, wherein the riboside is iPR or tZR.

16. The plant tissue culture of claim 12, wherein the gibberellic acid $A_3$ is present in the composition in a concentration of from about 1.0 µM to about 7.5 µM.

17. The composition of claim 1, wherein the culture medium is a gelled composition comprising DKW, tZR, water, and gibberellic acid $A_3$.

18. A plant tissue culture comprising a plant tissue from a Cannabaceae plant and a sterile gelled Cannabaceae growth composition comprising Driver Kuniyaki Walnut (DKW) medium, and the following:
(a) -6-(3,3-dimethylallylamino)-9-(3-D-ribofuranosylpurine (iPR),
(b) 6-(4-hydroxy-3-methylbutylamino)-9-(3-D-ribofuranosylpurine (DHZR),
(c) gibberellic acid $A_3$, and (d) 2,4-epi-brassinolide,
wherein the gelled composition is essentially free of auxins; and
wherein the gelled composition stimulates axillary shoot growth of the plant tissue to a greater extent than the Cannabaceae plant grown in the tissue culture without the composition.

19. A composition, comprising a plant tissue from a Cannabaceae plant and a gelled sterile culture medium comprising:
(a) Driver Kuniyaki Walnut (DKW) medium and at least one of 6-(3,3-dimethylallylamino)-9-(3-D-ribofuranosylpurine (iPR), and 6-(4-hydroxy-3-methylbutylamino)-9-(3-D-ribofuranosylpurine (DHZR),
(b) one or more of vitamins, carbohydrates, buffers, amino acids, salts, and gelling agents,
(c) gibberellic acid, and
(d) water,
wherein the gelled sterile culture medium has a pH of about 5.6 to 5.8 and comprises no auxins, and
wherein the gelled sterile culture medium stimulates axillary shoot growth of Cannabaceae grown in a tissue culture to a greater extent than Cannabaceae grown in the sterile tissue culture without the culture medium.

* * * * *